United States Patent
Herold et al.

(10) Patent No.: US 9,334,345 B2
(45) Date of Patent: May 10, 2016

(54) POLYMERIZABLE COMPOSITIONS CONTAINING (METH)ACRYLATE MONOMERS HAVING SULFIDE LINKAGES

(75) Inventors: Robert D. Herold, Monroeville, PA (US); Nina V. Bojkova, Monroeville, PA (US); Marvin J. Graham, Monroeville, PA (US); Charles R. Hickenboth, Cranberry Township, PA (US); Gregory J. McCollum, Gibsonia, PA (US); William H. Retsch, Jr., Allison Park, PA (US); Hongying Zhou, Allison Park, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 666 days.

(21) Appl. No.: 13/605,100

(22) Filed: Sep. 6, 2012

(65) Prior Publication Data
US 2013/0082220 A1  Apr. 4, 2013

Related U.S. Application Data

(60) Provisional application No. 61/532,275, filed on Sep. 8, 2011.

(51) Int. Cl.
| | |
|---|---|
| C08F 220/38 | (2006.01) |
| C08F 128/04 | (2006.01) |
| C07C 323/12 | (2006.01) |
| C08F 36/20 | (2006.01) |
| C09K 3/00 | (2006.01) |
| C08F 222/10 | (2006.01) |
| G02B 1/04 | (2006.01) |

(52) U.S. Cl.
CPC ............. *C08F 128/04* (2013.01); *C07C 323/12* (2013.01); *C08F 36/20* (2013.01); *C08F 220/38* (2013.01); *C08F 222/1006* (2013.01); *C09K 3/00* (2013.01); *G02B 1/04* (2013.01); *C08F 2220/382* (2013.01)

(58) Field of Classification Search
CPC .. C08F 220/38; C08F 220/382; C08F 128/04; C08F 128/02
See application file for complete search history.

(56) References Cited

U.S. PATENT DOCUMENTS

| | | | | |
|---|---|---|---|---|
| 4,429,092 | A | * | 1/1984 | Sterling .................. 526/192 |
| 4,939,218 | A | * | 7/1990 | Kawaki ............. C07C 323/12 351/159.01 |
| 5,789,476 | A | | 8/1998 | Iryo et al. |
| 5,811,503 | A | * | 9/1998 | Herold et al. .............. 526/323.2 |
| 5,916,987 | A | | 6/1999 | Kobayashi et al. |
| 6,194,511 | B1 | | 2/2001 | Momoda et al. |
| 2005/0261406 | A1 | | 11/2005 | Nakayama et al. |

FOREIGN PATENT DOCUMENTS

| | | |
|---|---|---|
| CN | 1414987 A | 4/2003 |
| JP | 4-11613 A | 1/1992 |
| JP | 2867638 B2 | 12/1998 |
| JP | 11125701 A | 5/1999 |
| JP | 11246626 A | 9/1999 |
| JP | 2000186120 A | 7/2000 |
| JP | 2001509522 A | 7/2001 |
| JP | 200282201 A | 3/2002 |
| JP | 2004536934 A | 12/2004 |
| JP | 2009102550 A | 5/2009 |
| WO | 01/36506 | 5/2001 |
| WO | 03011926 A1 | 2/2003 |
| WO | 2004009659 A1 | 1/2004 |
| WO | 2006068138 A1 | 6/2006 |

OTHER PUBLICATIONS

Novel curing agents: Thermal radical initiators as viable alternatives to peroxides. Studer et al. Progress in Organic Coatings 61 (2008) 119-125.*
Search Report dated May 14, 2014 for Taiwan Application No. 101132821.
Espacent English abstract of JP 2867638 B2, Dec. 1998.
Espacent English abstract of JP 4-11613 A, Jan. 1992.

* cited by examiner

*Primary Examiner* — Michael L Leonard
(74) *Attorney, Agent, or Firm* — The Webb Law Firm

(57) ABSTRACT

Provided is a polymerizable composition including (meth)acrylate monomers having at least two sulfide (—S—) linkages in the monomer. The polymerizable compositions include a first (meth)acrylate monomer represented by the following Formula (I),

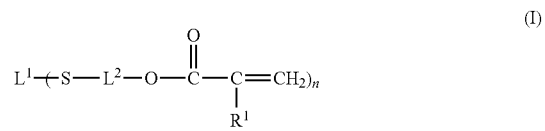

where $L^1$ is selected from a multivalent optionally substituted hydrocarbyl group optionally interrupted with at least one of —C(O)—, —S—, —O— and combinations thereof, and a divalent linking group represented by the following Formula (A).

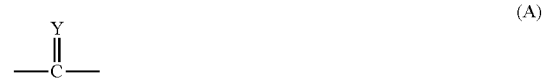

In Formula (A), Y is O or S. Also in Formula (I), $L^2$ is independently for each n a divalent optionally substituted hydrocarbyl group optionally interrupted with at least one of —O— and —S—, $R^1$ is independently selected for each n from hydrogen and methyl, and n is from 2 to 6. The polymerizable compositions also may include a polymerization moderator. Also provided are polymerizates including photochromic articles and optical elements prepared from such polymerizable compositions.

32 Claims, No Drawings

POLYMERIZABLE COMPOSITIONS CONTAINING (METH)ACRYLATE MONOMERS HAVING SULFIDE LINKAGES

CROSS-REFERENCE TO RELATED APPLICATIONS

The present application claims the benefit of priority from U.S. Provisional Application No. 61/532,275, filed Sep. 8, 2011, which is incorporated by reference herein in its entirety.

FIELD OF THE INVENTION

The present invention relates to polymerizable compositions that include (meth)acrylate functional monomers having at least two sulfide (—S—) linkages in the monomer, and to polymerizates prepared from such polymerizable compositions, such as optical lenses and photochromic articles.

BACKGROUND OF THE INVENTION

Polymeric materials, such as plastics, have been developed as alternatives and replacements for silica based inorganic glass in applications such as, optical lenses, fiber optics, windows and automotive, nautical and aviation transparencies. These polymeric materials can provide advantages relative to glass, including, shatter resistance, lighter weight for a given application, ease of molding and ease of dying. Representative examples of such polymeric materials include, poly (methyl methacrylate), polycarbonate and poly(diethylene glycol bis(allylcarbonate)).

The refractive indices of many polymeric materials are generally lower than that of high index glass. For example, the refractive index of poly(diethylene glycol bis(allylcarbonate)) is about 1.50, compared to that of high index glass, which can range, for example, from 1.60 to 1.80. When fabricating lenses to correct a given degree of visual defect, for example, a correction for myopia, the use of a polymeric material having a lower refractive index will require a thicker lens relative to a material having a higher refractive index, such as high index glass. If the degree of correction required is substantial, such as in the case of severe myopia, a lens fabricated from a low index polymeric material can become so thick as to negate any benefit of reduction in weight, as compared to an equivalent degree of correction provided by a higher refractive index lens, such as a high refractive index glass lens. In addition, thicker optical lenses generally are not aesthetically desirable.

Polymeric materials prepared from the polymerization of monomers containing aromatic rings typically have high refractive indices. Shaped articles, such as optical lenses, prepared from such high index polyaromatic materials, however, generally have lower ABBE numbers (also known as nu-values). Lower ABBE numbers are indicative of an increasing level of chromatic dispersion, which is typically manifested as an optical distortion at or near the rim of the lens. As such, optical materials having lower ABBE numbers are generally less desirable.

Polymeric materials having a combination of high refractive indices, such as at least 1.57, and low levels of chromatic dispersion (e.g., having ABBE numbers of at least 30), can be prepared from monomers containing certain heteroatoms, such as sulfur atoms. Such polymerizable compositions when polymerized with thermally activated catalysts can, however, undergo erratic and/or excessive rates of polymerization, which result in defects in the resulting polymerizates, such as visible lines, surface defects (e.g., dimples and/or craters), and/or cracks or fissures, within the body and/or through the surface of the polymerizate.

It would be desirable to develop polymerizable compositions that provide desirable optical properties, such as a combination of high refractive index and reduced chromatic dispersion. It would be further desirable that such newly developed polymerizable compositions are not subject to erratic and/or excessive rates of polymerization, and polymerizates prepared therefrom are free of defects resulting from such uncontrolled polymerization.

SUMMARY OF THE INVENTION

In accordance with the present invention, there is provided a polymerizable composition comprising, (a) at least one first (meth)acrylate functional monomer represented by the following Formula (I),

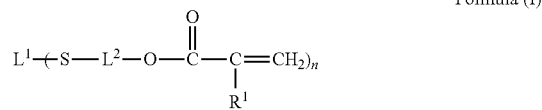

Formula (I)

With reference to Formula (I), $L^1$ is selected from at least one of, (i) a multivalent optionally substituted hydrocarbyl group optionally interrupted with at least one of —C(O)—, —S—, —O— and combinations thereof, and (ii) a divalent linking group represented by the following Formula (A),

Formula (A)

With reference to Formula (A), Y is O or S. With further reference to Formula (I): $L^2$ is independently for each subscript-n, a divalent optionally substituted hydrocarbyl group optionally interrupted with at least one of —O— and —S—; $R^1$ is independently selected, for each subscript-n, from hydrogen and methyl; and subscript-n is from 2 to 6. In addition to including the (meth)acrylate functional monomer represented by Formula (I), such polymerizable compositions according to the present invention also, optionally, may comprise, (b) a polymerization moderator.

In further accordance with the present invention, there is provided a polymerizable composition comprising, (a) at least one thio(meth)acrylate functional monomer represented by the following Formula (II).

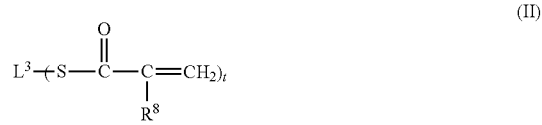

(II)

With reference to Formula (II): $L^3$ is a multivalent optionally substituted hydrocarbyl group optionally interrupted with at least one of —C(O)—, —S—, —O— and combinations thereof; $R^8$ is independently selected for each t from hydrogen and methyl; and t is from 2 to 6. In addition to including at least one thio(meth)acrylate monomer represented by Formula (II), the polymerizable composition also comprises (b)

at least one (meth)acrylate functional monomer represented by the following Formula (III).

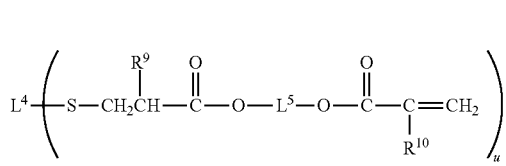

With reference to Formula (III): $L^4$ is a multivalent optionally substituted hydrocarbyl group optionally interrupted with at least one of —C(O)—, —S—, —O— and combinations thereof; $L^5$ is independently for each u a divalent optionally substituted hydrocarbyl group; $R^9$ and $R^{10}$ are each independently selected for each u from hydrogen and methyl; and u is from 2 to 6. With some embodiments, in addition to including (a) a thio(meth)acrylate functional monomer represented by Formula (II) and (b) a (meth)acrylate functional monomer represented by Formula (III), such polymerizable compositions according to the present invention can also optionally further comprise (c) a polymerization moderator.

In accordance with further embodiments of the present invention, there is provided, a polymerizable composition comprising: (a) at least one (meth)acrylate functional monomer represented by the following Formula (IV),

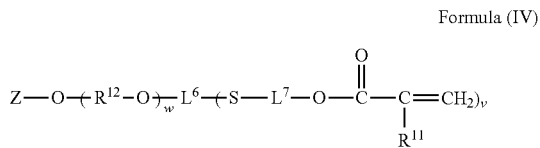

With reference to Formula (IV): $L^6$ is selected from a multivalent optionally substituted hydrocarbyl group; $L^7$ is independently for each v a divalent optionally substituted hydrocarbyl group optionally interrupted with at least one of —O— and —S—, $R^{11}$ is independently selected for each v from hydrogen and methyl, v is from 2 to 6; and $R^{12}$ is independently for each w divalent optionally substituted hydrocarbyl. With further reference to Formula (IV), w is 0 to 10, and Z is selected from hydrogen or a group represented by the following Formula (V),

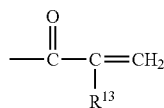

With reference to Formula (V), $R^{13}$ is hydrogen or methyl. In addition to the (meth)acrylate functional monomer represented by Formula (IV), such polymerizable compositions according to the present invention can, with some embodiments, optionally further comprise (b) a polymerization moderator.

DETAILED DESCRIPTION OF THE INVENTION

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), and copolymers (e.g., prepared from at least two monomer species).

As used herein, the term "(meth)acrylate" and similar terms, such as (meth)acryloyl and (meth)acrylic acid ester, means methacrylate and acrylate.

As used herein, the term "thio(meth)acrylate" and similar terms, such as thio(meth)acryloyl and thio(meth)acrylic acid ester, means thiomethacrylate and thioacrylate.

As used herein, recitations of "linear or branched" groups, such as linear or branched alkyl, are understood to include: a methylene group or a methyl group; groups that are linear, such as linear $C_2$-$C_{25}$ alkyl groups; and groups that are appropriately branched, such as branched $C_3$-$C_{25}$ alkyl groups.

As used herein, the term "halo" and similar terms, such as halo group, halogen, halogen group, halide, and halide group means F, Cl, Br and/or I, such as fluoro, chloro, bromo and/or iodo.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

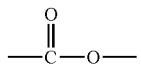

or equivalently —C(O)O—, is inclusive of the right-to-left representation thereof,

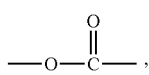

or equivalently —O(O)C— or —OC(O)—.

As used herein, the articles "a," "an," and "the" include plural referents unless otherwise expressly and unequivocally limited to one referent.

Other than in the operating examples, or where otherwise indicated, all numbers expressing quantities of ingredients, reaction conditions, and so forth used in the specification and claims are to be understood as modified in all instances by the term "about."

The monomers of the compositions of the present invention include groups, such as, but not limited to, multivalent and/or divalent $L^1$, $L^2$, $L^3$, $L^4$, $L^5$, $L^6$, $L^7$ and $L^8$ that can in each case be independently selected from optionally substituted hydrocarbyl. As used herein the term "hydrocarbyl" and similar terms, such as "hydrocarbyl substituent," means; linear or branched $C_1$-$C_{25}$ alkyl (e.g., linear or branched $C_1$-$C_{10}$ alkyl); linear or branched $C_2$-$C_{25}$ alkenyl (e.g., linear or branched $C_2$-$C_{10}$ alkenyl); linear or branched $C_2$-$C_{25}$ alkynyl (e.g., linear or branched $C_2$-$C_{10}$ alkynyl); $C_3$-$C_{18}$ cycloalkyl, including poly-fused-ring cycloalkyl, and polycycloalkyl (e.g., $C_3$-$C_{10}$ cycloalkyl); $C_5$-$C_{18}$ aryl, including polycyclic or poly-fused-ring aryl (e.g., $C_5$-$C_{10}$ aryl); and $C_6$-$C_{24}$ aralkyl (e.g., $C_6$-$C_{10}$ aralkyl).

As used herein the term "hydrocarbyl" is inclusive of "heterohydrocarbyl," which is a hydrocarbyl in which at least one carbon, but less than all of the carbons thereof, has been replaced with a heteroatom, such as, but not limited to, O, N, S, and combinations thereof. Examples of heterohydrocarbyls from which a hydrocarbyl can be selected include, but are not limited to: $C_3$-$C_{18}$ heterocycloalkyl (having at least one hetero atom in the cyclic ring), including poly-fused-ring heterocycloalkyl, and polycyclicheteroalkyl; and $C_5$-$C_{18}$ heteroaryl (having at least one hetero atom in the aromatic ring), including polycyclic or poly-fused-ring heteroaryl.

Representative alkyl groups include but are not limited to methyl, ethyl, propyl, isopropyl, butyl, isobutyl, sec-butyl, tert-butyl, pentyl, neopentyl, hexyl, heptyl, octyl, nonyl, decyl, and structural isomers thereof. Representative alkenyl groups include but are not limited to vinyl, allyl, propenyl, butenyl, pentenyl, hexenyl, heptenyl, structural isomers thereof, related species thereof containing two or more ethylenically unsaturated groups. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative poly-fused-ring cycloalkyl groups include but are not limited to decahydronaphthalenyl, tetradecahydroanthracenyl, and tetradecahydrophenanthrenyl. Representative polycyclicalkyl groups include but are not limited to bicyclo [2.2.1]heptanyl (norbornyl), and bicyclo[2.2.2]octanyl. Representative heterocycloalkyl groups include but are not limited to tetrahydrofuranyl, tetrahydropyranyl and piperidinyl, including but not limited to piperidin-4-yl. Representative polycyclicheterocycloalkyl groups include but are not limited to, 7-thiabicyclo[2.2.1]heptanyl, 7-oxabicyclo[2.2.1]heptanyl, and 7-azabicyclo[2.2.1]heptanyl. Representative aryl groups include but are not limited to phenyl, biphenyl, naphthyl, anthracenyl, phenanthrenyl and triptycenyl. Representative heteroaryl groups include but are not limited to furanyl, pyranyl and pyridinyl. Representative aralkyl groups include but are not limited to benzyl, and phenethyl.

As used herein, the term "optionally substituted" with regard to groups, including but not limited to, hydrocarbyl groups, alkyl groups, cycloalkyl groups, and aryl groups, means a group, including but not limited to, a hydrocarbyl group, alkyl group, cycloalkyl group, and/or aryl group, in which at least one hydrogen thereof has been replaced or substituted with a group that is other than hydrogen, such as, but not limited to, halo groups (e.g., F, Cl, I, and Br), hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (including, but not limited to: alkyl; alkenyl; alkynyl; cycloalkyl, including poly-fused-ring cycloalkyl and polycyclocalkyl; heterocycloalkyl; aryl, including hydroxyl substituted aryl, such as phenol, and including poly-fused-ring aryl; heteroaryl, including poly-fused-ring heteroaryl; and aralkyl groups), and amine groups, such as —N($R^{11'}$)($R^{12'}$) where $R^{11'}$ and $R^{12'}$ are each independently selected from hydrogen, hydrocarbyl and substituted hydrocarbyl.

For purposes of non-limiting illustration, the hydrocarbyl, of a substituted hydrocarbyl, can be selected from one or more of the hydrocarbyl groups described previously herein, such as a linear or branched $C_1$-$C_{25}$ alkyl group, which can be substituted with one or more of the substituting groups described previously herein, such as one or more $C_3$-$C_{12}$ cycloalkyl groups and/or one or more $C_5$-$C_{18}$ aryl groups, for example, an ethyl group substituted with a cyclohexyl group and/or a phenyl group.

The optionally substituted groups, including but not limited to, optionally substituted hydrocarbyl groups, optionally substituted alkyl groups, optionally substituted cycloalkyl groups, and optionally substituted aryl groups, from which the various groups described herein can each be independently selected, such as, but not limited to, multivalent and/or divalent linking groups $L^1, L^2, L^3, L^4, L^5, L^6, L^7$ and $L^8$ can in each case be independently and optionally interrupted with at least one of —C(O)—, —S—, —O— and combinations thereof, or at least one of —O— and —S—, as the case may be. As used herein, by interrupted with at least one of —C(O)—, —S—, and —O—, or at least one of —O— and —S—, means that at least one carbon of, but less than all of the carbons of, the optionally substituted group (such as optionally substituted hydrocarbyl groups, optionally substituted alkyl groups, optionally substituted cycloalkyl groups, and optionally substituted aryl groups) is in each case independently replaced with one of the recited divalent non-carbon linking groups. The optionally substituted groups (such as optionally substituted hydrocarbyl groups, optionally substituted alkyl groups, optionally substituted cycloalkyl groups, and optionally substituted aryl groups) can be interrupted with two or more of the above recited linking groups, which can be adjacent to each other or separated by one or more carbons. For purposes of non-limiting illustration, a combination of adjacent —C(O)— and —O— can provide a divalent carboxylic acid ester linking or interrupting group, —C(O)—O—. For purposes of further non-limiting illustration, a combination of adjacent —C(O)— and —S— can provide a divalent thiocarboxylic acid ester linking or interrupting group, —C(O)—S—. For purposes of additional non-limiting illustration, a combination of adjacent —O—, —C(O)— and —O— can provide a divalent carbonate linking or interrupting group, —O—C(O)—O—.

Additionally or alternatively, as used herein, by interrupted with at least one of —C(O)—, —S—, and —O—, or at least one of —O— and —S—, means that the various groups from which, for example, multivalent and/or divalent linking groups $L^1, L^2, L^3, L^4, L^5, L^6, L^7$ and $L^8$ can in each case be independently selected, can be separated or interrupted with at least one of —C(O)—, —S—, and —O—, or at least one of —O— and —S—, as the case may be. For purposes of non-limiting illustration, when $L^1$ is selected from, or composed of, two or more groups, such as a multivalent linear or branched optionally substituted $C_1$-$C_{25}$ alkyl Group and a multivalent optionally substituted $C_3$-$C_{12}$ cycloalkyl group, the multivalent groups can be interrupted with at least one of —C(O)—, —S—, —O— and combinations thereof. For purposes of further non-limiting illustration, a linking group, such as $L^1$, can, with some embodiments, be selected from both a divalent ethyl group (such as, ethan-1,2-diyl, —CH$_2$—CH$_2$—) and a divalent cyclohexyl group (such as, cyclohexan-1,4-diyl,

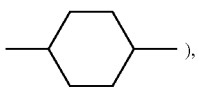

which can be interrupted by at least one of —C(O)—, —S—, —O— and combinations thereof. For purposes of additional non-limiting illustration, a divalent ethyl group (such as, ethan-1,2-diyl, and a divalent cyclohexyl group (such as, cyclohexan-1,4-diyl,

interrupted with —S—, can be represented by the following Formula (E),

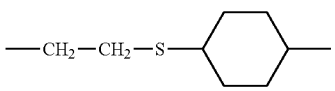

Formula (E)

As used herein, the term "multivalent" with regard to multivalent linking groups, means a group that has at least two covalent bonds that serve to link the linking group to two or more substituents or portions of the compound or monomer. As used herein, the term 'divalent' with regard to divalent linking groups, means a group that has two covalent bonds that serve to link the linking group to two substituents or portions of the compound or monomer.

The monomers of the polymerizable compositions of the present invention as described herein, including monomers represented by Formula (I), Formula (II), Formula (III), Formula (IV) and related monomers, in each case optionally further include one or more coproducts that include one or more radically polymerizable ethylenically unsaturated groups, such as, but not limited to oligomers that include one or more radically polymerizable ethylenically unsaturated groups, resulting from the synthesis of such monomers. The coproducts, such as oligomeric coproducts, can optionally also be present in the polymerizable compositions of the present invention.

The polymerizable compositions of the present invention, including the monomers thereof, for example as represented by Formula (I), and the various groups thereof will be described in further detail herein as follows.

With reference to Formula (I), and with some embodiments, $L^1$ can be selected from multivalent linear or branched optionally substituted $C_1$-$C_{25}$ alkyl, multivalent optionally substituted $C_3$-$C_{12}$ cycloalkyl, multivalent optionally substituted aryl, and combinations thereof optionally interrupted with at least one of —C(O)—, —S—, —O— and combinations thereof. Each group from which $L^1$ can be selected can itself optionally be interrupted with at least one of —C(O)—, —S—, —O— and combinations thereof. Additionally or alternatively, and as discussed previously herein, when $L^1$ is selected from, or composed of, two or more groups, such as a multivalent linear or branched optionally substituted $C_1$-$C_{25}$ alkyl group and a multivalent optionally substituted $C_3$-$C_{12}$ cycloalkyl group, the multivalent groups can be interrupted with at least one of —C(O)—, —S—, —O— and combinations thereof.

The divalent group $L^2$ of Formula (I), with some embodiments, can be selected from divalent optionally substituted linear or branched $C_1$-$C_{25}$ alkyl, divalent optionally substituted $C_3$-$C_{12}$ cycloalkyl, divalent optionally substituted aryl, and combinations thereof optionally interrupted with at least one of —O— and —S—.

According to some embodiments, $L^1$ of Formula (I) is selected from multivalent linear or branched $C_1$-$C_{10}$ alkyl optionally interrupted with at least one of —C(O)—, —S— and —O—. In accordance with some additional embodiments, $L^2$ of Formula (I) is independently for each n selected from divalent linear or branched $C_1$-$C_{10}$ alkyl optionally interrupted with at least one —O—. Examples of multivalent and divalent alkyl groups from which $L^1$ and $L^2$ can each be independently selected, include, but are not limited to, methyl, ethyl, propyl, butyl, pentyl, hexyl, heptyl, octyl, nonyl, and decyl, including structural isomers thereof.

The multivalent $L^1$ linking group of the first (meth)acrylate functional monomer represented by Formula (I), with some embodiments, is selected from multivalent linear or branched $C_1$-$C_{10}$ alkyl interrupted with at least one —S— group, and n of Formula (I) is 2 or 3. The multivalent linear or branched $C_1$-$C_{10}$ alkyl groups from which $L^1$ can be selected include, but are not limited to, those recited previously herein.

The multivalent $L^1$ linking group of Formula (I), with some embodiments, is a divalent linking group, n is 2, and $L^1$ is represented by the following Formula (B),

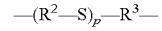  Formula (B)

With reference to Formula (B), $R^2$ for each p is independently selected from divalent linear or branched optionally substituted $C_1$-$C_{10}$ alkyl, and/or divalent optionally substituted $C_3$-$C_{12}$ cycloalkyl. With further reference to Formula (8), $R^3$ is selected from divalent linear or branched optionally substituted $C_1$-$C_{10}$ alkyl, and/or divalent optionally substituted $C_3$-$C_{12}$ cycloalkyl, and p is 0 to 10. The divalent alkyl groups from which $R^2$ and $R^3$ can each be independently selected include, but are not limited to, those described previously herein with regard to $L^1$.

Non-limiting examples of divalent optionally substituted linear or branched alkyl groups from which $R^2$ for each p and $R^3$ can each be independently selected include, but are not limited to: —CH$_2$—; —CH$_2$CH$_2$—; —CH(Ph)CH$_2$—, where Ph represents optionally substituted phenyl (—C$_6$H$_5$); —(CH$_2$)$_3$—; —CH(CH$_3$)CH$_2$—; —(CH$_2$)$_4$—; —CH(CH$_3$)CH$_2$CH$_2$—; —CH$_2$CH(CH$_3$)CH$_2$—; —C(CH$_3$)$_2$CH$_2$—; —(CH$_2$)$_3$—; —CH(CH$_3$)CH$_2$CH$_2$CH$_2$—; —CH$_2$CH(CH$_3$)CH$_2$CH$_2$—; —C(CH$_3$)$_2$CH$_2$CH$_2$—; and —CH$_2$C(CH$_3$)$_2$CH$_2$—.

Non-limiting examples of divalent optionally substituted cycloalkyl groups from which $R^2$ for each p and $R^3$ can each be independently selected include, but are not limited to cyclopropan-1,1-diyl; cyclopropan-1,2-diyl; cyclobutan-1,1-diyl; cyclobutan-1,2-diyl; cyclobutan-1,3-diyl; cyclopentan-1,1-diyl; cyclopentan-1,2-diyl; cyclopentan-1,3-diyl; cyclohexan-1,1-diyl; cyclohexan-1,2-diyl; cyclohexan-1,3-diyl; and cyclohexan-1,4-diyl.

With the preceding non-limiting examples of divalent optionally substituted linear or branched alkyl groups and divalent optionally substituted cycloalkyl groups from which $R^2$ for each p and $R^3$ can each be independently selected, one or more hydrogens thereof can each be optionally and independently substituted or replaced with a group other than hydrogen including, but not limited to, those groups as described previously herein with regard to the term "optionally substituted."

The divalent group $L^2$ of Formula (I) can, in accordance with some embodiments, be represented by the following Formula (C), $$-(R^4-O)_q-R^5-$$  Formula (C)

With reference to Formula (C): $R^4$ for each q is independently selected from linear or branched optionally substituted $C_1$-$C_{10}$ alkyl, and optionally substituted $C_3$-$C_{12}$ cycloalkyl; $R^5$ is selected from linear or branched optionally substituted $C_1$-$C_{10}$ alkyl, and optionally substituted $C_3$-$C_{12}$ cycloalkyl; and q is 0 to 10.

Non-limiting examples of divalent optionally substituted divalent linear or branched alkyl groups from which $R^4$ for each q and $R^5$ can each be independently selected include, but are not limited to, those described previously herein with regard to $R^2$ and $R^3$, in which one or more hydrogens thereof can each be optionally and independently substituted or replaced with a group other than hydrogen including, but not limited to, those groups as described previously herein with regard to the term "optionally substituted." Non-limiting examples of divalent optionally substituted cycloalkyl groups from which $R^4$ for each q and $R^5$ can each be independently selected include, but are not limited to those described previously herein with regard to $R^2$ and $R^3$, in which one or more hydrogens thereof can each be optionally and independently replaced with a group other than hydrogen including, but not limited to, those groups as described previously herein with regard to the term "optionally substituted."

In accordance with some embodiments, n of Formula (I) is 2, $L^1$ is represented by Formula (B) and $L^2$ is represented by Formula (C), in which case the first (meth)acrylate functional monomer can be represented by the following Formula (Ia):

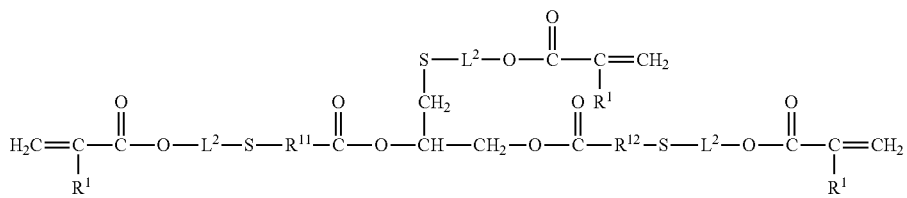

Formula (Ia)

With reference to Formula (Ia), $R^1$, $R^2$, $R^3$, $R^4$, $R^5$, p, and q are each independently as described previously herein. The first (meth)acrylate functional monomer represented by Formula (Ia) includes at least two sulfide linkages (—S—).

With further reference to Formula (Ia), and with some embodiments of the present invention: p is 1; each q is independently 0 to 10, provided that at least one q is at least 1; $R^2$, $R^3$, $R^4$ and $R^5$ are each divalent ethyl, such as ethan-1,2-diyl; and each $R^1$ is independently hydrogen or methyl.

With additional reference to Formula (Ia), and in accordance with some embodiments: p is 1 each q is 0; and $R^2$, $R^3$ and $R^5$ are each selected from divalent ethyl, such as ethan-1,2-diyl, in which case the first (meth)acrylate functional monomer can be represented by the following Formula (Ib):

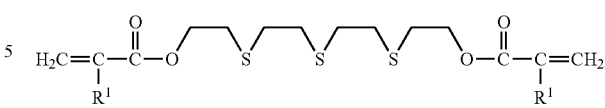

Formula (Ib)

With reference to Formula (Ib), each $R^1$ is independently selected from hydrogen and methyl, as described previously herein.

With some embodiments, $L^1$ of Formula (I) is selected from a trivalent group represented by the following Formula $L^1$(a).

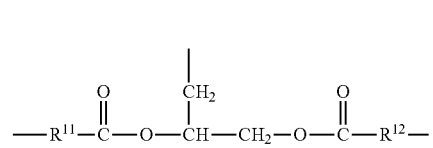

Formula $L^1$(a)

With reference to Formula $L^1$(a), and with some embodiments, $R^{11}$ and $R^{12}$ are each independently selected from: divalent linear or branched alkyl, such as divalent linear or branched $C_1$-$C_{25}$ alkyl, or divalent linear or branched $C_1$-$C_{10}$ alkyl, or divalent linear or branched $C_1$-$C_4$ alkyl, or divalent $C_1$-$C_2$ alkyl; divalent cyclic alkyl, such as divalent $C_5$-$C_8$ cyclic alkyl; divalent phenyl, including linear or branched $C_1$-$C_9$ alkyl substituted divalent phenyl. When $L^1$ is selected from a trivalent group represented by Formula $L^1$(a), n of Formula (I) is 3.

When $L^1$ is selected from a trivalent group represented by Formula $L^1$(a), the first (meth)acrylate functional monomer represented by Formula (I) can be represented by the following Formula (Ic);

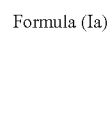

Formula (Ic)

With reference to Formula (Ic), each $R^1$ and each $L^2$ are each independently as described previously herein.

The first (meth)acrylate functional monomer of the polymerizable compositions of the present invention, for example, as represented by Formula (I), can be prepared by art-recognized methods. With some embodiments, and for purposes of non-limiting illustration, the first (meth)acrylate functional monomer represented by Formula (I) can be prepared by reaction of one mole of a polythiol having n thiol groups (—SH) and at least n moles of one or more oxirane functional materials (and/or one or more cyclic ethers), which results in the formation of a hydroxyl functional intermediate having n hydroxyl groups, where n, in each case, is as described with reference to Formula (I). Examples of oxirane functional materials include, but are not limited to, alkylene oxides, such as ethylene oxide and propylene oxide. Alternatively, the polythiol can be reacted with a 2-halo-1-hydroxy-alkane, such as 2-chloroethanol, in accordance with art-recognized methods. Further alternatively, the polythiol can be reacted with a 1,2-alkylene carbonate, such as ethylene carbonate, in accordance with art-recognized methods. Reaction of the polythiol with oxirane functional material, or 2-halo-1-hydroxy-alkane, or 1,2-alkylene carbonate, results in the formation of a hydroxyl functional intermediate.

The hydroxyl functional intermediate can then be reacted with a (meth)acrylic acid ester with the concurrent removal of alcohol, thereby resulting in formation of a first (meth)acrylate functional monomer represented by Formula (I). Alternatively, the hydroxyl functional intermediate can be reacted with a (meth)acryloyl halide, such as (meth)acryloyl chloride, with subsequent work-up procedures to remove the resulting hydrogen halide and/or salt thereof. Further alternatively, the hydroxyl functional intermediate can be reacted with (meth)acrylic anhydride, in accordance with art-recognized methods. The hydroxyl functional intermediate also can be reacted with (meth)acrylic acid with concurrent removal of water, thereby resulting in formation of a first (meth)acrylate functional monomer represented by Formula (I).

When $L^1$ is represented by Formula (A), and for purposes of non-limiting illustration, the first (meth)acrylate functional monomer represented by Formula (I) can be prepared by reaction of a carbonic dihalide (when Y of Formula A is O) or a carbonothioic dihalide (when Y of Formula A is S) with two moles of a thiol functional material represented by the following Formula (F):

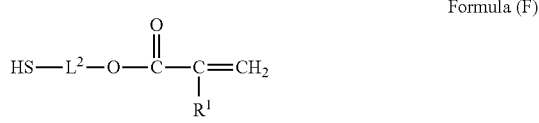

Formula (F)

With reference to Formula (F), $L^2$ and $R^1$ are each as described previously herein with regard to Formula (I).

Alternatively, when $L^1$ is represented by Formula (A), and for purposes of further non-limiting illustration, the first (meth)acrylate functional monomer represented by Formula (I) can be prepared by reaction of N,N-carbonyldiimidazole (when Y of Formula A is O) or a N,N-thiocarbonyldiimidazole (when Y of Formula A is S) with two moles of a thiol functional material represented by Formula (F).

With reference to Formula (I), and in accordance with some embodiments, n is 2, $L^1$ is selected from a divalent linking group represented by Formula (A), and $L^2$ is represented by the following Formula (B),

Formula (B)

With reference to Formula (B), $R^2$ for each p, and $R^3$ are each independently as described previously herein, and p is 0 to 10.

When n is 2, $L^1$ is represented by Formula (A) and $L^2$ is represented by Formula (B), and for purposes of non-limiting illustration, the first (meth)acrylate functional monomer represented by Formula (I) can be prepared by reaction of a carbonic dihalide (when Y of Formula A is O) or a carbonothioic dihalide (when Y of Formula A is S) with a dithiol, such as dimercaptodiethylsulfide (which can also be equivalently referred to as bis(2-mercaptoethyl)sulfide), which results in the formation of an intermediate dithiol having a —C(O)— or —C(S)— linkage in the backbone thereof. The intermediate dithiol is then reacted with two moles of an oxirane functional material, such as ethylene oxide, which results in the formation of di-hydroxy functional intermediate. The di-hydroxy functional intermediate can then be reacted with two moles of a (meth)acrylate with the concurrent removal of a 2 moles of alcohol, which results in formation of a first (meth)acrylate functional monomer. In the preceding general synthetic procedure, the carbonic dihalide can be replaced with N,N-carbonyldiimidazole (when Y of Formula A is O), and/or the carbonothioic dihalide can be replaced with N,N-thiocarbonyldiimidazole ('her Y of Formula A is S). With further reference to the preceding general synthetic procedure, the (meth)acrylate reactant can be replaced with a (meth)acryloyl halide, such as (meth)acryloyl chloride.

With reference to Formula (I), and with some embodiments, n is 4, and $L^1$ is selected from, a divalent linking group represented by the following Formula (D),

Formula (D)

With reference to Formula (O), $R^6$ and $R^7$ are each independently selected from hydrogen, linear or branched optionally substituted $C_1$-$C_{10}$ alkyl, optionally substituted $C_3$-$C_{12}$ cycloalkyl, and optionally substituted aryl. Alternatively, $R^6$ and $R^7$ together form a $C_4$-$C_{12}$ optionally substituted cycloalkyl.

With further reference to Formula (I), with some embodiments, when n is 2 and $L^1$ is represented by Formula (D), $L^2$ is represented by, the following Formula (B),

Formula (B)

With reference to Formula (B), $R^2$ for each p, and $R^3$ are each independently as described previously herein, and p is 0 to 10.

When, as with some embodiments, $L^1$ is represented by Formula (O), $L^2$, with some embodiments, is represented by Formula (B), and n is 2, the first (meth)acrylate functional monomer represented by Formula (I) can be represented by the following Formula (Id),

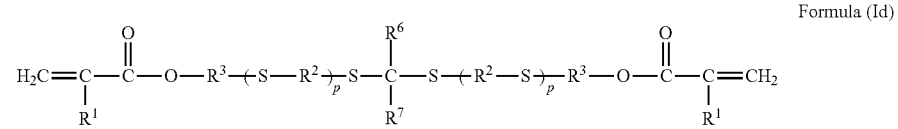

Formula (Id)

With reference to Formula (Id), $R^1$, $R^2$, $R^3$, $R^6$, $R^7$, and each p are each independently as described previously herein. With further reference to Formula (Id), and with some embodiments of the present invention, each $R^1$ is independently selected from hydrogen and methyl, $R^6$ and $R^7$ are each independently selected from hydrogen and methyl, $R^2$ and $R^3$ are in each case ethan-1,2-diyl, and each p is independently 1 or 2.

With reference to Formula (I), when $L^1$ is represented by Formula (D), $L^2$ is represented by Formula (B), and n is 2, the first (meth)acrylate monomer of the polymerizable compositions of the present invention can be prepared by art-recognized methods. For purposes of non-limiting illustration, a first (meth)acrylate functional monomer represented by Formula (Id) can be prepared in accordance with the following representative Scheme-(A).

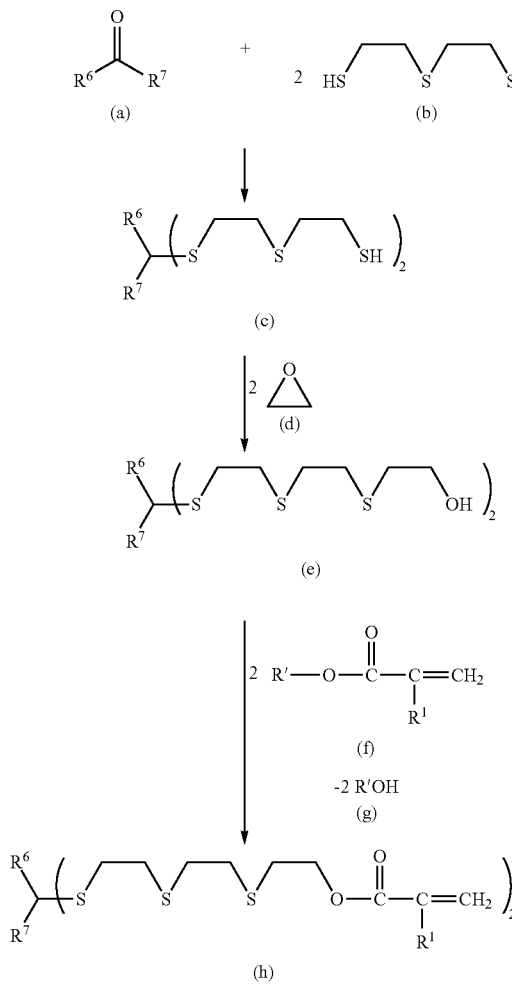

With reference to Scheme-(A), $R^1$, $R^6$, and $R^7$ are each as described previously herein with reference to, for example, Formula (Id), and R' is a monovalent hydrocarbyl, such as linear or branched $C_1$-$C_{25}$ alkyl, or $C_3$-$C_{12}$ cycloalkyl. With further reference to Scheme-(A), 1 mole of an aldehyde or ketone (a) is reacted with 2 moles of a di-thiol, such as dimercaptodiethylsulfide (b) (which can also be equivalently referred to as bis(2-mercaptoethyl)sulfide), which results in formation of a thiol functional adduct (c). Thiol functional adduct (c) is reacted with 2 moles of an oxirane functional material, such a ethylene oxide (d), which results in formation of a hydroxy functional intermediate (e). Hydroxy functional intermediate (e) is reacted with 2 moles of a (meth)acrylate (f) with the concurrent removal of 2 moles of alcohol (g), which results in formation of a first (meth)acrylate functional monomer (h), which can be used in the polymerizable compositions of the present invention.

With further reference to Scheme-(A), the formation of thiol functional adduct (c) can be accompanied by the concurrent formation of coproducts, such as oligomeric coproducts. The formation of oligomeric coproducts can be minimized by adjusting the relative molar amounts of the aldehyde/ketone (a) and dithiol (b). For purposes of non-limiting illustration, a molar ratio of dithiol (b) to aldehyde/ketone (a) of at least 4 to 1 typically results in minimal formation of oligomeric coproduct.

With additional reference to Scheme-(A), the (meth)acrylate (f) can be replaced with a (meth)acryloyl halide, such as (meth)acryloyl chloride, in which case 2 moles of hydrogen halide, such as hydrogen chloride, would be generated, rather than 2 moles of alcohol (g). The first (meth)acrylate monomer (h) would be separated from the hydrogen halide in accordance with art-recognized work-up procedures.

With further additional reference to Scheme-(A), the aldehyde or ketone (a) can be replaced with an acetal or a ketal (a-1) represented by the following Formula (5-1).

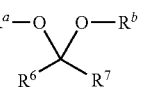

Formula (a-1)

With reference to Formula (a-1), $R^6$ and $R^7$ are each as described previously herein, and Fr and Rb are each independently selected from linear or branched optionally substituted $C_1$-$C_{25}$ alkyl, optionally substituted $C_3$-$C_{12}$-cycloalkyl, and optionally substituted aryl. The aldehyde or ketone (a) of Scheme-(A) can, with some embodiments, be replaced with an equimolar amount of acetal/ketal represented by Formula (a-1). For purposes of non-limiting illustration, with some embodiments, the acetal ketal represented by Formula (a-1) is acetone dimethylketal.

With further reference to Formula (I) and in accordance with some embodiments, n is 2, and $L^1$ is a divalent linking group represented by Formula (Gel) as described in further detail below. The divalent linking group $L^8$ of Formula (G-1) is, with some embodiments, a residue of a hydrocarbyl group having two non-conjugated carbon-carbon double bonds. With some embodiments, $L^8$ of Formula (G-1) is a residue of vinyl-cyclohexene, and $L^8$ is represented by Formula (G-2) as described in further detail below, and $L^1$ of Formula (I) is represented by Formula (G-3) as described in further detail below.

The polymerizable compositions of the present invention can, in addition to the first (meth)acrylate functional monomer represented by Formula (I), further include at least one thio(meth)acrylate functional monomer represented by the following Formula (II),

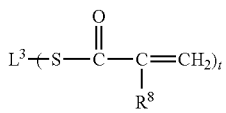
(II)

With reference to Formula (II), and as discussed previously herein, $L^3$ is a multivalent optionally substituted hydrocarbyl group optionally interrupted with at least one of —C(O)—, —S—, —O— and combinations thereof. Each $R^8$ group of Formula (II) is independently selected for each t from hydrogen and methyl, and t is from 2 to 6.

The groups from which $L^3$ of the thio(meth)acrylate functional monomer represented by Formula (II) can be selected include, but are not limited to, those groups described previously herein with regard to $L^1$ of Formula (I). With some embodiments of the present invention, the multivalent $L^3$ group of Formula (II) is selected from multivalent linear or branched optionally substituted $C_1$-$C_{25}$ alkyl, multivalent optionally substituted $C_3$-$C_{12}$ cycloalkyl, multivalent optionally substituted aryl, and combinations thereof optionally interrupted with at least one of —C(O)—, —S—, —O— and combinations thereof.

With some embodiments, t is 2, and $L^3$ of Formula (II) is represented by Formula (B), as described previously herein, and the thio(meth)acrylate monomer can be represented by the following Formula (IIa).

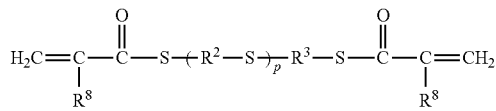
Formula (IIa)

With reference to Formula (IIa), $R^2$, $R^3$, $R^8$ and p are each independently as described previously herein.

With some embodiments of the present invention, and with further reference to Formula (IIa), p is 1, and $R^2$ and $R^3$ are each divalent ethyl, such as ethan-1,2-diyl, in which case the thio(meth)acrylate functional monomer represented by Formula (IIa) can be represented by the following Formula (IIb).

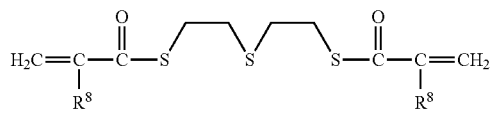
Formula (IIb)

With reference to Formula (IIb), each $R^8$ is independently selected from hydrogen and methyl, as described previously herein.

Thio(meth)acrylate monomers represented by Formula (II) can be prepared by art-recognized methods. For purposes of non-limiting illustration, a polythiol, such as such as dimercaptodiethylsulfide, or a salt of a polythiol, such as such as dimercaptodiethylsulfide disodium salt, can be reacted with a (meth)acryloyl halide, such as (meth)acryloyl chloride, which results in the formation of a thio(meth)acrylate functional monomer represented by Formula (II), or, for example, Formula (IIa).

With further reference to Formula (II) and with some embodiments, t is 2, and $L^3$ is represented by the following Formula (G-1).

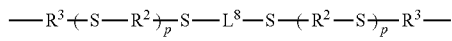
Formula (G-1)

With reference to Formula (G-1), $R^2$, $R^3$ and p are in each case as independently described previously herein with regard to Formula (B). With further reference to Formula (G-1), $L^8$ is a divalent optionally substituted hydrocarbyl. With some embodiments, $L^8$ is selected from divalent linear or branched optionally substituted $C_1$-$C_{25}$ alkyl, divalent optionally substituted $C_3$-$C_{12}$ cycloalkyl, divalent optionally substituted aryl, and combinations thereof.

The divalent group $L^8$ of Formula (G-1) with some embodiments is a residue of an optionally substituted hydrocarbyl having two non-conjugated carbon-carbon double bonds, such as a linear or branched optionally substituted $C_1$-$C_{25}$ alkyl having two non-conjugate double bonds, and/or optionally substituted $C_3$-$C_{12}$ cycloalkyl having two non-conjugated double bonds. With some embodiments, $L^8$ of Formula (G-1) is a residue of vinyl-cyclohexene, such as 4-vinyl-1-cyclohexene or 3-vinyl-1-cyclohexene. In accordance with some non-limiting embodiments, $L^6$ of Formula (G-1) is a residue of vinyl-cyclohexene, and is represented by the Following (G-2),

Formula (G-2)

In accordance with some embodiments, and with reference to Formula (II), t is 2, and $L^3$ is represented by Formula (G-1), in which $L^8$ is a residue of vinyl-cyclohexene and is represented by Formula (G-2), in which case $L^3$ is more particularly represented by the following Formula (G-3),

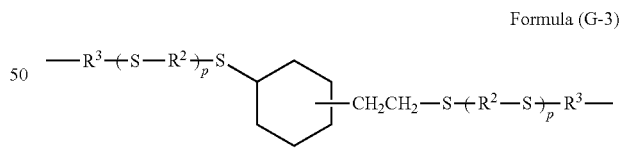
Formula (G-3)

With reference to Formula (G-3), and in accordance with some embodiments, the two groups bonded to the cyclohexane ring are ortho, meta or para relative to each other, and are not bonded to the same carbon of the cyclohexane ring. With further reference to Formula (G-3), $R^2$, $R^3$ and p independently in each case are described previously herein with regard to Formula (B).

Further, when t is 2 and $L^3$ is represented by Formula (G-3) in which the two groups bonded to the cyclohexane ring are para relative to each other, the thio(meth)acrylate monomer represented by Formula (II) can be more particularly represented by the following Formula (IIc).

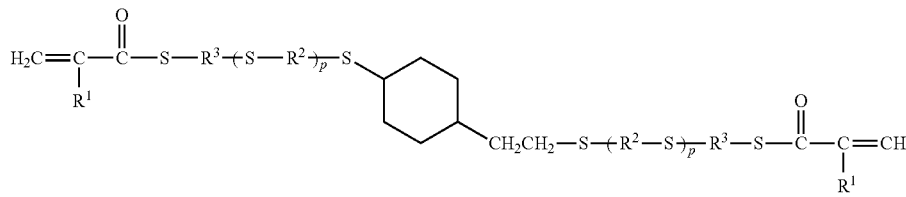

Formula (IIc)

In accordance with some embodiments, when t is 2 and $L^3$ is represented by Formula (G-3) in which the two groups bonded to the cyclohexane ring are meta relative to each other, the thio(meth)acrylate monomer represented by Formula (II) can be more particularly represented by the following Formula (IId).

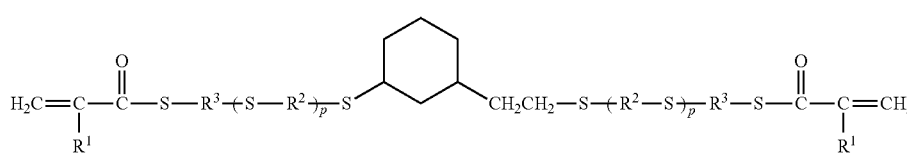

Formula (IId)

With reference to Formulas (IIc) and (IId), each $R^1$ is independently selected from hydrogen and methyl, and $R^2$, $R^3$ and p are each independently as described previously herein with regard to Formula (B).

With additional reference to Formulas (IIc) and (IId), and with some embodiments, $R^2$ and $R^3$ are each ethan-1,2-diyl, and each p is 1, in which case the thio(meth)acrylate monomers represented by Formulas (IIc) and (IId) can be represented by the following Formulas (IIe) and (IIf), respectively.

For purposes of non-limiting illustration, thiol-ene reactions generally involve the reaction of a material having one or more thiol groups, such as a dithiol, with a material having one or more carbon-carbon double bonds, such as a vinyl compound, a (meth)acrylate, and/or an allyl compound. With some embodiments, a material having one or more carbon-carbon triple bonds is used, as described in further detail herein with regard to the synthesis of monomers represented by Formula (IV). For free radical initiated thiol-ene reactions, reaction between the material having one or more thiol groups and the material having one or carbon-carbon double bonds is typically carried out in the presence of a free radical initiator, such as peroxide type and/or azo type free radical initiators. Examples of peroxide free radical initiators include, but are not limited to: peroxymonocarbonate esters, such as tertiary-

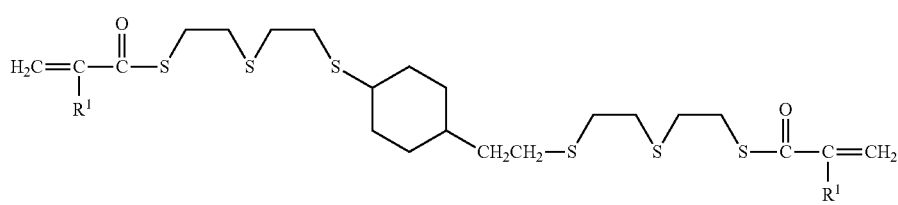

Formula (IIe)

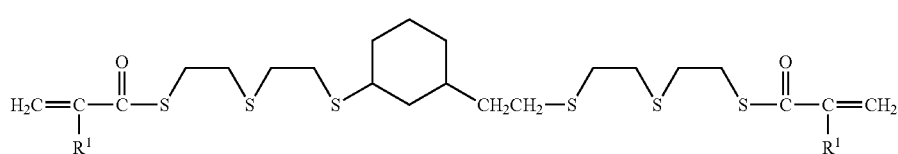

Formula (IIf)

Thio(meth)acrylate functional monomers similar to those represented by Formulas (IIc) and (IId) can be prepared by art-recognized methods. For purposes of non-limiting illustration, 2 moles of a dithiol, such as dimercaptodiethylsulfide, are reacted with one mole of vinyl-cyclohexene, such as 4-vinyl-1-cyclohexene, under art-recognized thiol-ene reaction conditions, which results in a thiol-functional intermediate. The thiol-functional intermediate(s) is/are then reacted with 2 moles of a (meth)acryloyl halide, such as (meth)acryloyl chloride, resulting in formation of a thio(meth)acrylate functional monomer represented by Formula (IIe), or Formula (IIf), or mixtures thereof.

butylperoxy 2-ethylhexyl carbonate and tertiarybutylperoxy isopropyl carbonate; peroxyketals, such as 1,1-di-(t-butyl peroxy)-3,3,5-trimethylcyclohexane; peroxydicarbonate; esters, such as di(2-ethylhexyl)peroxydicarbonate, di(secondary butyl)peroxydicarbonate and diisopropylperoxydicarbonate; diacyperoxides, such as 2,4-dichlorobenzoyl peroxide, isobutyryl peroxide, decanoyl peroxide, lauroyl peroxide, propionyl peroxide, acetyl peroxide, benzoyl peroxide, p-chlorobenzoyl peroxide; peroxyesters such as t-butylperoxy pivalate, t-butylperoxy octylate, and t-butylperoxyisobutyrate; methylethylketone peroxide, and acetylcyclohexane sulfonyl peroxide. Examples of suitable azo type radical initiators include, but are not limited to, azobis(organonitrile) compounds, such as azobis(isobutyronitrile) and azobis(2,4-dimethylvaleronitrile). Additional non-limiting examples of azo type radical initiators are described in further detail herein with regard to the synthesis of monomers represented by Formula (IV). The free radical initiator is typically present in an amount at least sufficient to initiate reaction between the thiol compound and the compound containing one or more carbon-carbon double bonds. With some embodiments, the free radical initiator is present in an amount of from 0.01 percent by weight to 5 percent by weight, based on weight of reactants. The thiol-ene reaction can be conducted under any suitable temperature, such as from room temperature (e.g., about 25° C.) to 100° C. The reaction temperature typically depends at least in part on the temperature or temperature range under which the free radical initiator is thermally activated.

When the reactants are multifunctional, such as a polythiol having two or more thiol groups and a material having two or more carbon-carbon double bonds, the thiol-ene reaction can result in the formation of some oligomeric species. With some embodiments, the formation of oligomeric species can be minimized by adjusting the molar ratio of the reactants. For purposes of non-limiting illustration, with the reaction between a dithiol and a material having two carbon-carbon double bonds (that are reactive with thiol groups), the dithiol can be present in a molar excess relative to the material having two carbon-carbon double bonds, such as a molar ratio of greater than or equal to 2:1, or greater than or equal to 3:1, or greater than or equal to 4:1.

It should be understood that for purposes of the present invention, "base catalyzed thiol-ene reaction" conditions are the preferred conditions of thiol-ene reaction of a thiol compound with a material having (meth)acrylate group(s). Base catalysts that can be used for these purposes include base catalysts known to those skilled in the art; tertiary amines, including but not limited to triethylamine, 1,8-diazabicyclo [5.4.0]undec-7-ene, 1,5-diazabicyclo[4.3.0]non-5-ene, and 1,4-diazabicyclo[2.2.2]octane, and tertiary phosphines, including but not limited to trioctylphosphine, tributylphosphine, triphenylphosphine, methyldiphenylphosphine, and dimethylphenylphosphine.

The polymerizable compositions according to some embodiments of the present invention can optionally include, in addition to the first (meth)acrylate functional monomer represented by Formula (I), at least one second (meth)acrylate functional monomer represented by the following Formula (III).

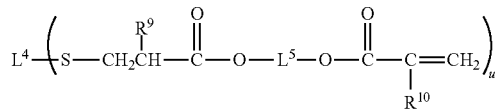

Formula (III)

With reference to Formula (III) and as described previously herein, $L^4$ is a multivalent optionally substituted hydrocarbyl group optionally interrupted with at least one of —C(O)—, —S—, —O— and combinations thereof. With further reference to Formula (III), $L^5$ is independently for each u a divalent optionally substituted hydrocarbyl group. The $R^9$ and $R^{10}$ groups of Formula (III) are each independently selected for each u from hydrogen and methyl, and u is from 2 to 6.

The multivalent linking group $L^4$ of Formula (III) can be selected from those classes and examples of multivalent linking groups described previously herein with reference to $L^1$ of Formula (I). The divalent linking groups $L^5$ of Formula (III) can be selected from those classes and examples of divalent linking groups described previously herein with reference to $L^2$ of Formula (I).

The multivalent linking group $L^4$ of Formula (III) can with some embodiments, be selected from multivalent linear or branched optionally substituted $C_1$-$C_{25}$ alkyl, multivalent optionally substituted $C_3$-$C_{12}$ cycloalkyl, multivalent optionally substituted aryl, and combinations thereof optionally interrupted with at least one of —C(O)—, —S—, —O— and combinations thereof. With some embodiments, u of Formula (III) is 2 and the multivalent linking group $L^4$ is a divalent linking group, which can be represented by Formula (B), as described previously herein with regard to Formula (I).

The divalent linking groups $L^5$ of Formula (III), with some embodiments, can each be independently selected for each u from: divalent linear or branched optionally substituted $C_1$-$C_{25}$ alkyl, or divalent linear or branched optionally substituted $C_1$-$C_{10}$ alkyl, or divalent linear or branched optionally substituted $C_1$-$C_4$ alkyl, or divalent optionally substituted $C_1$-$C_2$ alkyl; divalent optionally substituted $C_3$-$C_{12}$ cycloalkyl, such as such as divalent optionally substituted $C_5$-$C_8$ cyclic alkyl; divalent optionally substituted aryl, such as divalent phenyl, including linear or branched $C_1$-$C_9$ alkyl substituted divalent phenyl; and combinations thereof. The divalent linking group $L^5$ of Formula (III) can, with some embodiments, be represented by Formula (C), as described previously herein with regard to Formula (I).

The second (meth)acrylate functional monomer represented by Formula (III) can be prepared by art-recognized methods. For purposes of non-limiting illustration, when u is 2, a polythiol, such as dimercaptodiethylsulfide is reacted with a bis-(meth)acrylate, such as alkyleneglycol bis(meth)acrylate including, but not limited to, ethyleneglycol bis(meth)acrylate, or, polyalkyleneglycol bis(meth)acrylate including, but not limited to, diethyleneglycol bis(meth)acrylate, under base catalyzed thiol-ene reaction conditions, which results in formation of a second (meth)acrylate functional monomer represented by Formula (III). Synthesis of the second (meth)acrylate functional monomer represented by Formula (III) can result in the formation of coproducts, such as oligomeric coproducts, which can optionally be present in the polymerizable compositions of the present invention.

In accordance with some embodiments, and with reference to Formula (III), u is 2, and $L^4$ is represented by Formula (G-1) and more particularly by Formula (G-3), as described previously herein. When u is 2 and $L^4$ is represented by Formula (G-1) or more particularly by Formula (G-3), $L^5$ of Formula (III) is, with some embodiments represented by Formula (C), as described previously herein with regard to Formula (I). Such a Formula (III) type (meth)acrylate monomer can be prepared by art-recognized methods. For purposes of non-limiting illustration, 2 moles of a dithiol, such as dimercaptodiethylsulfide, are reacted with one mole of vinyl-cyclohexene, such as 4-vinyl-1-cyclohexene or 3-vinyl-1-cyclohexene, under free radical thiol-ene reaction conditions, which results in a thiol-functional intermediate. The thiol-functional intermediate is then reacted with a bis(meth)acrylate, such as alkyleneglycol bis(meth)acrylate or polyalkyleneglycol bis(meth)acrylate, under base catalyzed thiol-ene reaction conditions, which results in formation of a second (meth)acrylate functional monomer represented by Formula (III), in which $L^4$ is represented by Formula (G-1) or more particularly by Formula (G-3), and $L^5$ is represented by Formula (C).

The polymerizable compositions of the present invention include, with some embodiments, a (meth)acrylate monomer represented by Formula (I) and at least one of a thio(meth) acrylate monomer represented by Formula (II) and/or a (meth)acrylate monomer represented by Formula (III). When composed of a (meth)acrylate monomer represented by Formula (I) and at least one further monomer represented by Formulas (II) and/or (III), the (meth)acrylate monomer represented by Formula (I) is present, with some embodiments, in an amount of from 1 to 99 percent by weight, or from 20 to 90 percent by weight, or from 40 to 80 percent by weight, and the further monomer represented by Formula (II) and/or Formula (III) is present in a combined amount of from 1 to 99 percent by weight, or from 10 to 75 percent by weight, or from 20 to 60 percent by weight, the percent weights in each case being based on total weight of the recited monomers.

In accordance with some embodiments, and as described previously herein, the polymerizable compositions include at least one thio(meth)acrylate functional monomer represented by Formula (II) and at least one meth(acrylate) functional monomer represented by Formula (III). The monomers represented by Formulas (II) and (III) are each independently as described previously herein. With some embodiments, the polymerizable composition comprising monomers represented by Formulas (II) and (III), is free of (meth)acrylate functional monomers represented by Formula (I). The relative amounts of monomers represented by Formulas (II) and Formula (III) can vary widely. In accordance with some embodiments, the thio(meth)acrylate functional monomer(s) represented by Formula (II) are present in an amount of from 20 to 99 percent by weight, or from 35 to 90 percent by weight, or from 50 to 80 percent by weight, and the (meth) acrylate functional monomer(s) represented by Formula (III) is present in an amount of from 1 to 80 percent by weight, or from 10 to 65 percent by weight, or from 20 to 50 percent by weight, the percent weights in each case being based on the total weight of the recited monomers. As previously mentioned, any of the polymerizable compositions of the present invention described immediately above also may further comprise a polymerization moderator as described herein below.

The polymerizable compositions of the present invention can include, with some embodiments, at least one diethylenically unsaturated monomer chosen from, 1,2-divinylbenzene, 1,3-divinylbenzene, 1,4-divinylbenzene, bisphenol A ethoxylate diacrylate (CAS #64401-02-1), bisphenol A ethoxylate dimethacrylate (CAS #41637-38-1), bisphenol A propoxylate diacrylate (CAS #67952-50-5), bisphenol A propoxylate dimethacrylate. Bisphenol A glycerolate diacrylate (CAS #4687-94-9), bisphenol A glycerolate dimethacrylate (CAS #1565-94-2), bisphenol F ethoxylate diacrylate (CAS #120750-67-6), bisphenol F ethoxylate dimethacrylate, bisphenol F propoxylate diacrylate, bisphenol F propoxylate dimethacrylate, bisphenol S ethoxylate diacrylate, bisphenol S ethoxylate dimethacrylate, bisphenol S propoxylate diacrylate, bisphenol S propoxylate dimethacrylate, polyethylene glycol di(meth)acrylate, polypropylene glycol di(meth)acrylate, (meth)acrylic anhydride, or mixtures thereof. The concentrations of the aforementioned co-monomers, individually or in combination, range from 0.5% to 60%, based upon the total monomer weight of the polymerizable composition. The effect of the material on refractive index and other properties of the finished polymer is taken into consideration regarding the amount used individually or in combination.

Further, the polymerizable compositions of the present invention also can include at least one polyethylenically unsaturated monomer chosen from trimethylolpropane tri (meth)acrylate, trimethylolethane tri(meth)acrylate, ditrimethylolpropane tetra(meth)acrylate, pentaerythritol tri(meth) acrylate, pentaerythritol tetra(meth)acrylate, dipentaerythritol penta(meth)acrylate, di(pentaerythritol hexa(meth)acrylate, tris(2-hydroxyethyl)tri(meth)acrylate, 2,4,6-triallyloxy-1,3,5-triazine (CAS #101-37-1), 1,3,5-triallyl-1,3,5-triazine-2,4,6(1H,3H,5H)-trione (CAS #1025-15-6), or mixtures thereof. The concentrations of the aforementioned co-monomers, individually or in combination, range from 0.1% to 20%, based upon the total monomer weight of the polymerizable composition. The effect of the material on refractive index and other properties of the finished polymer is taken into consideration regarding the amount used individually or in combination.

With some embodiments, the polymerizable compositions of the present invention include at least one (meth)acrylate functional monomer represented by Formula (IV), as described previously herein. The multivalent $L^6$ and divalent $L^7$ groups of Formula (N) can be selected from those groups as described previously herein with regard to $L^1$ and $L^2$ of Formula (I), respectively. With some embodiments of the present invention, the multivalent $L^6$ group of Formula (IV) is selected from multivalent linear or branched optionally substituted $C_1$-$C_{25}$ alkyl, multivalent optionally substituted $C_3$-$C_{12}$ cycloalkyl, multivalent optionally substituted aryl, and combinations thereof optionally interrupted with at least one of —C(O)—, —S—, —O— and combinations thereof. In accordance with additional embodiments, the divalent $L^7$ group of Formula (IV) is independently for each v selected from divalent linear or branched optionally substituted $C_1$-$C_{25}$ alkyl, divalent optionally substituted $C_3$-$C_{12}$ cycloalkyl, divalent optionally substituted aryl, and combinations thereof optionally interrupted with at least one of —O— and —S—.

With further reference to Formula (IV), with some embodiments of the present invention, the divalent $R^{12}$ group can be selected, independently for each w, from those groups as described previously herein with regard to $R^4$ of Formula (C). With some embodiments, each $R^{12}$, of Formula (IV), for each w is independently selected from divalent linear or branched optionally substituted $C_1$-$C_{10}$ alkyl, and divalent optionally substituted $C_{12}$ cycloalkyl.

With further reference to Formula (IV) and in accordance with some embodiments, v is 2, and $L^6$ is a trivalent residue of a hydroxyl functional compound having a single carbon-carbon triple bond. Examples of hydroxyl functional compounds having a single carbon-carbon triple bond from which the (meth)acrylate functional monomer represented by Formula (IV) can be prepared include, but are not limited to, propargyl alcohol, 2-butyne-1,4-diol, 3-butyne-2-ol, 3-hexyne-2,5-diol, and mixtures of two or more thereof. A portion of the hydroxyl functional groups on the hydroxyl functional compound having a single carbon-carbon triple bond may be esterified. For example, a portion of the hydroxyl functional compound having a single carbon-carbon triple bond may include an alkyne-functional ester of a $C_1$-$C_{12}$ carboxylic acid such as propargyl acetate, propargyl propionate, propargyl benzoate, and the like.

When v is 2 and $L^6$ is a trivalent residue of a hydroxyl functional compound having a single carbon-carbon triple bond, the (meth)acrylate monomer represented by Formula (IV) can be prepared in accordance with the following general description with propargyl alcohol as the hydroxyl functional compound having a single carbon-carbon triple bond. Typically, a thiol functional intermediate is first formed by reacting 1 mole of propargyl alcohol with about two moles of a dithiol, such as dimercaptodiethylsulfide, under art-recognized free radical thiol-ene reaction conditions. The dithiol groups can each form a covalent bond with one carbon of the C—C triple bond group, or with both carbons of the C—C triple bond group. While not intending to be bound by any theory, it is believed that one dithiol group forms a covalent bond with each separate carbon of the C—C triple bond. The resulting thiol functional intermediate is reacted with at least 2 moles, such as 2 to 3 moles of an oxirane functional material, such as ethylene oxide, or a cyclic ether, which results in the formation of a hydroxyl functional intermediate. Alternatively, said thiol functional intermediate can be reacted with at least 2 moles, such as 2 to 3 moles, of a 2-halo-1-hydroxylalkane, such as 2-chlorethanol, in accordance with art-recognized method, thus forming a hydroxyl functional intermediate. Likewise, the thiol functional intermediate can be reacted with at least 2 moles, such as 2 to 3 moles, of a 1,2-alkylene carbonate, such as ethylene carbonate, in accordance with art-recognized methods, this forming a hydroxyl functional intermediate. The hydroxyl functional intermediate is then reacted with at least 2 moles, such as 2 to 6 moles of a (meth)acrylate with concurrent removal of alcohol, so as to result in formation of the (meth)acrylate functional monomer represented by Formula (IV). Alternatively, the hydroxyl functional intermediate can be reacted with at least 2 moles, such as 2 to 3 moles, of a (meth)acryloyl halide, such as (meth)acryloyl chloride, which results in formation of the (meth)acrylate functional monomer represented by Formula (IV), after art-recognized work-up procedures to separate the desired product from the resulting hydrogen halide. Formation of the thiol functional intermediate can result in the concurrent formation of oligomeric species, which can optionally be present in combination with the (meth)acrylate functional monomer represented by Formula (IV).

During formation of some (meth)acrylate functional monomers represented by Formula (IV), formation of the thiol functional intermediate as described previously herein, can be carried out in the presence of a free-radical initiator. The free-radical initiator can be selected from art-recognized compounds. Non-limiting examples of free-radical initiators include, but are not limited to, azo or peroxide type free-radical initiators, such as azobisalkalenenitriles. The free-radical initiator can be selected from azobisalkalenenitriles, which are commercially available from DuPont under the tradename VAZO. Examples of VAZO initiators that can be used include, but are not limited to VAZO 52 VAZO-64, VAZO 67, VAZO-88 initiators, and mixtures thereof. Preparation of the thiol functional intermediate is described in further detail in U.S. Pat. No. 7,888,436 B2 at column 8, lines 3-53, which disclosure is incorporated herein by reference.

With some embodiments of the present invention, polymerizable compositions that include at least one (meth)acrylate functional monomer represented by Formula (IV), can further include at least one monomer selected from monomers represented by Formula (I), Formula (II), Formula (III), and combinations of two or more thereof. When the polymerizable composition is, with some embodiments, composed of a (meth)acrylate monomer represented by Formula (IV) and at least one further monomer represented by Formulas (I), (II) and/or (III), the (meth)acrylate monomer represented by Formula (IV) is present in an amount of from 1 to 99 percent by weight, or from 25 to 95 percent by weight, or from 50 to 90 percent by weight, and the further monomer represented by Formulas (I), (II) and/or (III) is present in a combined amount of from 1 to 99 percent by weight, or from 5 to 75 percent by weight, or from 10 to 50 percent by weight, the percent weights in each case being based on the total weight of the recited monomers.

In accordance with some non-limiting embodiments, the polymerizable compositions of the present invention include a (meth)acrylate monomer represented by Formula (IV) and a (meth)acrylate monomer represented by Formula (I), in which $L^1$ of the (meth)acrylate monomer represented by Formula (I) is free of substitution with a group represented by the following Formula (M):

Formula (M)

With reference to Formula (M), Z, $R^{12}$ and w are each as described previously herein with regard to Formula (IV).

In a particular embodiment, the present invention is directed to a polymerizable composition comprising:

(a) at least one thio(meth)acrylate functional monomer represented by the following Formula (IIg),

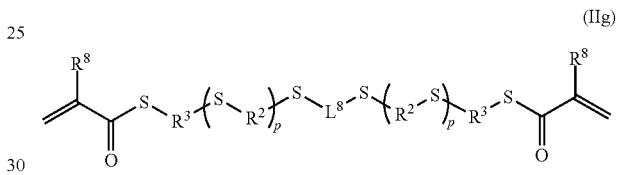

(IIg)

wherein, $L^6$ is a divalent linking group selected from,
(i) a divalent linking group represented by the following Formula (O),

—C($R^6$)($R^7$)— (D)

wherein $R^6$ and $R^7$ each independently are selected from hydrogen, linear or branched optionally substituted $C_1$-$C_{10}$ alkyl, optionally substituted $C_3$-$C_{12}$ cycloalkyl, and optionally substituted aryl, or $R^6$ and $R^7$ together form a $C_4$-$C_{12}$ optionally substituted cycloalkyl, and (ii) a divalent linking group represented by the following Formula (A);

(A)

wherein Y is O or S, and $R^2$ for each p is independently selected from divalent linear or branched optionally substituted $C_1$-$C_{10}$ alkyl, and/or divalent optionally substituted $C_3$-$C_{12}$ cycloalkyl, each $R^3$ independently is selected from divalent linear or branched optionally substituted $C_1$-$C_{10}$ alkyl, and/or divalent optionally substituted $C_3$-$C_{12}$ cycloalkyl, each p is from 0 to 10, each $R^8$ is independently selected from hydrogen and methyl; and (b) optionally a polymerization moderator.

The monomers of the compositions of the present invention, such as the monomers represented by Formula (I), (II), (III) and (IV), can be prepared, as described previously herein, from polythiols having two or more thiol groups. Examples of polythiols that can be used to prepare the monomers of the polymerizable compositions of the present invention, such as, but are not limited to, monomers represented by Formula (I), Formula (II), Formula (III), Formula (IV) and related monomers, include, but are not limited to, 1,2-ethanedithiol, 2,2'-thiodiethanethiol, 2,5-dimercaptomethyl-1,4-dithiane, 1,2-bis-(2-mercaptoethylthio)-3-mercaptopropane, pentaerythritol tetrakis(3-mercaptopropionate), pentaerythritol tetrakis(2-mercaptoacetate), tetrakis(7-mercapto-2,5-dithiaheptyl)methane, trimethylolpropane tris(3-mercaptopropionate), trimethylolpropane tris(2-mercaptoacetate), 4-mercaptomethyl-3,6-dithia-1,8-octanedithiol, 4-tert-butyl-1,2-benzenedithiol, 4,4'-thiodibenzenethiol, benzenedithiol, ethylene glycol di(2-mercaptoacetate), ethylene glycol di(3-mercaptopropionate), poly(ethylene glycol) di(2-mercaptoacetate), poly(ethylene glycol) di(3-mercaptopropionate), a polythiol monomer represented by the following Formula (K),

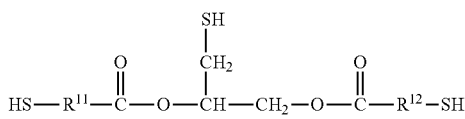

Formula (K)

With reference to Formula (K), $R^{11}$ and $R^{12}$ are each independently as described previously herein with reference to Formula $L^1$(a) A polythiol represented by Formula (K) can be prepared by an art-recognized esterification or transesterification reaction between, for example, 3-mercapto-1,2-propanediol (Chemical Abstract Service (CAS) Registry No, 96-27-5) and a thiol functional carboxylic acid or thiol functional carboxylic acid ester in the presence of a strong acid catalyst, such as methane sulfonic acid, with the concurrent removal of water or alcohol from the reaction mixture. The polythiol represented by Formula (K) optionally further includes coproducts, such as oligomers which can optionally include disulfide (—S—S—) linkages, resulting from its synthesis.

A non-limiting example of another dithiol that can be used to prepare the monomers of the compositions of the present invention is represented by the following Formula (N-1).

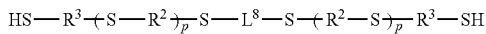

Formula (N-1)

With reference to Formula (N-1) $R^2$, $R^3$ and p are each independently as described previously herein with regard to Formula (B). With further reference to Formula (N-1), $L^3$ is as described previously herein with regard to Formulas (G-1), (G-2) and (G-3).

With some embodiments, and as described previously herein with regard to Formula (G-1), (G-2) and (G-3), $L^8$ is a residue of a optionally substituted hydrocarbyl having two non-conjugated carbon-carbon double bonds, such as vinylcyclohexene. The monomers of the polymerizable compositions of the present invention can, with some embodiments, be prepared using a dithiol represented by the following Formula (N-2),

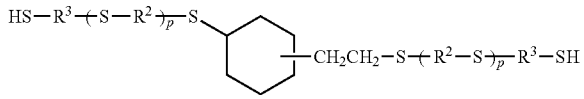

Formula (N-2)

With reference to Formula (N-1), $R^2$, $R^3$ and p are each independently as described previously herein with reference to Formula (B). With some embodiments, the two groups bonded to the cyclohexane, ring of Formula (N-2) are ortho, meta or para relative to each other, and are not bonded to the same carbon of the cyclohexane ring.

In some particular embodiments of the present invention, $L^2$ of Formula (I); $L^7$ of Formula (IV); $R^3$ of Formula (Id); $R^4/R^5$ of Formula (Ia); and $L^2$ of Formula (Ic) are each a divalent hydrocarbyl group centering one carbon atom, such as —$CH_2$—, —CH(R)—, or —C($R^1$)($R^2$)— where each of R, $R^1$ and $R^2$ independently represents an optionally substituted hydrocarbyl group. For example, such a monomer, where $L^2$ of Formula (I) is —$CH_2$—, car be synthesized by reacting 1 molar equivalent of mercaptan with 1 molar equivalent of formaldehyde (such as paraformaldehyde) resulting in an intermediate containing terminal hemithioacetal groups. This OH-terminated molecule then can be (meth)acrylated, either by reaction with (meth)acryloyl chloride or (meth)acrylic anhydride; direct esterification with (meth)acrylic acid; or by transesterification with an alkyl(meth)acrylate (such as methyl(meth)acrylate). Alternatively, the mercaptan can be reacted with a substituted aldehyde (HC(=O)R) instead of formaldehyde. For example, when mercaptan is reacted with benzaldehyde, $L^2$ would represent —CH(R)—, where R is phenyl.

In a further embodiment of the present invention, each of $L^2$ of Formula (I); $L^7$ of Formula (IV) and $R^3$ of Formula (Id) can be a divalent optionally substituted hydrocarbyl group, where the optional substitution is an aryl group, such as a phenyl group. For example, $L^2$ of Formula (I) can be —$CH_2$CH(R)— or —CH(R)—$CH_2$—, where R represents a phenyl group. This reaction product can result from the reaction of 1 molar equivalent of mercaptan with 1 molar equivalent of styrene oxide (through ring opening of the epoxide ring), to form a poly-hydroxy terminated sulfur-containing material with aromatic rings, followed by formation of (meth)acrylate end groups through the reaction of the terminal OH groups with either (meth)acryloyl chloride or (meth)acrylic anhydride, direct esterification with (meth)acrylic acid, or by transesterification with an alkyl(meth)acrylate.

Any of the polymerizable compositions of the present invention optionally can include, one or more monomers having a single ethylenically unsaturated radically polymerizable group. Examples of monomers having a single ethylenically unsaturated radically polymerizable group that can optionally be present in the polymerizable compositions of the present invention include, but are not limited to: acrylic acid; methacrylic acid; esters of acrylic acid such as methyl or ethyl acrylate and 2-hydroxyethyl acrylate; esters of methacrylic acid, such as methyl or ethyl methacrylate, phenoxyethyl methacrylate, isobornyl methacrylate, cyclohexyl methacrylate and 2-hydroxyethyl methacrylate; allyl esters, allyl benzoate; allyl carbonates, e.g., phenyl allyl carbonate; vinyl esters such as vinyl acetate; styrene; and vinyl chloride; ethylenically unsaturated carboxylic acid anhydrides, e.g., maleic anhydride, citraconic anhydride, and itaconic anhydride. More specifically, for example, the monoethylenically unsaturated monomers can include, methyl methacrylate, methacrylic acid, maleic anhydride, phenoxyethyl methacrylate, styrene and mixtures thereof. The monoethylenically unsaturated monomer(s), when used, is typically present in an amount of from 0.1 percent by weight to 60 percent by weight, based on the total monomer weight of the polymerizable composition, such as from 1 percent by weight to 55 percent by weight, or from 3 to 45 percent by weight, based on the total monomer weight of the polymerizable composition. The effect of the material on refractive index and other properties of the finished polymer is taken into consideration regarding the amount used individually or in combination.

The polymerizable compositions of the present invention further can include, with some embodiments, a polymerization moderator. The presence of polymerization moderator can minimize the formation of any distortions or defects, e.g., striations and or cracks/fissures, in polymerizates that may be obtained from the polymerizable compositions of the present invention. Examples of polymerization moderators that can be included in the polymerizable compositions of the present invention, include but are not limited to, dilauryl thiodipropionate, 1-isopropyl-4-methyl-1,4-cyclohexadiene (γ-terpinene); 1-isopropyl-4-methyl-1,3-cyclohexadiene (α-terpinene); 1-methyl-4-(propan-2-ylidene)cyclohex-1-ene, (terpinolene); and alpha-methyl styrene dimer, 1,1-diphenylethylene, cis-1,2-diphenylethylene, 3,7,7-trimethylbicyclo[4.1.0]hept-3-ene (3-carene), 4-isopropenyl-1-methylcyclohexene (dipentene), (S)-(+4-isopropenyl-1-methylcyclohexene ((S)-limonene), 2,6-dimethyl-2,4,6-octatriene, 4-tert-butylpyrocatechol, triphenylmethane, and mixtures of two or more thereof.

With some embodiments, the polymerization moderator is selected from 1-isopropyl-4-methyl-1,4-cyclohexadiene; 1-isopropyl-4-methyl-1,3-cyclohexadiene; 1-methyl-4-(propan-2-ylidene)cyclohex-1-ene; 2,6-dimethyl-2,4,6-octatriene, and alpha-methyl styrene dimer.

As used herein, the term "alpha-methyl styrene dimer" means a polymerization moderator that includes 2,4-diphenyl-4-methyl-1-pentene, and optionally at least one of 2,4-diphenyl-4-Methyl-2-pentene and/or 2-phenyl-1-propene (which is also referred to as, alpha-methyl styrene). With some embodiments, the alpha-methyl styrene dimer polymerization moderator includes 90 to 93 percent by weight of 2,4-diphenyl-4-methyl-1-pentene, 6 to 8 percent by weight of 2,4-diphenyl-4-methyl-2-pentene, and 0.25 to 0.75 percent by weight of 2-phenyl-1-propene, the percent weights in each case being based on total weight of alpha-methyl styrene dimmer.

The polymerization moderator can be present in the polymerizable compositions of the present invention in a wide range of amounts. In some embodiments, the polymerization moderator is present in the polymerizable compositions of the present invention, in an amount from 0.01 percent to 15 percent by weight, or from 0.1 percent to 8 percent by weight, or from 0.3 percent to 5 percent by weight, based on the total weight of monomers and polymerization moderator.

The polymerizable compositions of the present invention can further include, with some embodiments, an initiator that is capable of initiating free radical polymerization of and amongst the ethylenically unsaturated groups of the monomers thereof. With some embodiments, the polymerizable compositions of the present invention include a free radical initiator that is thermally activated. By "thermally activated" means the free radical initiator becomes active at elevated temperature, such as at temperatures greater than ambient room temperature, such as greater than 25 C, as will be described in further detail herein.

The thermally activated free radical initiator can, with some embodiments, be selected from organic peroxy compounds, azobis(organonitrile) compounds, N-acyloxyamine compounds, O-imino-isourea compounds, and combinations of two or more thereof.

With some embodiments, the thermally activated free radical initiator is selected from one or more organic peroxy compounds. Examples of organic peroxy compounds, that may be used as thermal polymerization initiators include, but are not limited to: peroxymonocarbonate esters, such as tertiarybutylperoxy 2-ethylhexyl carbonate and tertiarybutylperoxy isopropyl carbonate; peroxyketals, such as 1,1-di-(t-butyl peroxy)-3,3,5-trimethylcyclohexane; peroxydicarbonate esters, such as di(2-ethylhexyl)peroxydicarbonate, di(secondary butyl)peroxydicarbonate and diisopropylperoxydicarbonate; diacyperoxides, such as 2,4-dichlorobenzoyl peroxide, isobutyryl peroxide, decanoyl peroxide, lauryl peroxide, propionyl peroxide, acetyl peroxide, benzoyl peroxide, p-chlorobenzoyl peroxide; peroxyesters such as t-butylperoxy pivalate, t-butylperoxy octylate, and t-butylperoxyisobutyrate; methylethylketone peroxide, and acetylcyclohexane sulfonyl peroxide.

With some embodiments, further examples of peroxy compounds from which the free radical initiator can be selected include, but are not limited to, 2,5-dimethyl-2,5-di(2-ethylhexanoylperoxy)hexane, and/or 1,1-bis(tert-butylperoxy)-3,3,5-trimethylcyclohexane.

Examples of azobis(organonitrile) compounds, that may be used as thermal polymerization initiators in the polymerizable compositions of the present invention, include, but are not limited to, azobis(isobutyronitrile), 2,2'-azobis(2-methylbutanenitrile), and/or azobis(2/1-dimethylvaleronitrile).

With some further embodiments of the present invention, the thermally activated free radical initiator is selected from 1-acetoxy-2,2,6,6-tetramethylpiperidine, and/or 1,3-dicyclohexyl-O—(N-cyclohexylideneamino)-isourea.

The amount of thermal polymerization initiator used to initiate and polymerize the polymerizable compositions of the present invention can vary, and can depend at least in part on the particular initiator or initiators used. With some embodiments, only that amount that is required to initiate and sustain the polymerization reaction is required, which can be referred to as an initiating amount. With some embodiments, the thermally activated free radical initiator is present in an amount of from 0.01 to 7 parts of initiator, or from 0.1 to 3.5 parts initiator, or from 0.5 to 2.5 parts initiator, in each case the part, initiator being per 100 parts of monomer(s) (phm) present in the polymerizable composition.

The thermal cure cycle used to cure the polymerizable compositions of the present invention, with some embodiments, involves heating the polymerizable composition in the presence of the initiator from room temperature up to 50° C. to 150° C., over a period of from 2 hours to 48 hours, or from 30° C. up to 90° C. or 100° C. over a period of from 12 to 24 hours, or from 65° C. up to 115° C. or 125° C. over a period of from 12 to 24 hours.

Polymerization of the polymerizable compositions of the present invention results in the formation of a polymerizate, which can be in the form of a shaped article. Polymerizates obtained from polymerization of the polymerizable compositions of the present invention are solid, and with some embodiments, transparent. Transparent polymerizates prepared from the polymerizable compositions of the present invention, can be used in optical or ophthalmic applications.

Polymerize es prepared from the polymerizable compositions of the present invention, with some embodiments, have: a refractive index of at least 1.57, or at least 1.58, or at least 1.59; an ABBE number of at least 30, or at least 33, or at least 35; and a Fischer microhardness value of at least 50 N/mm$^2$, or at least 70 N/mm$^2$, or at least 90N/mm$^2$. With some embodiments, polymerizates prepared from the polymerizable compositions of the present invention have an initial (zero second) Barcol hardness of at least 1, or at least 10, or at least 20. The refractive index, ABBE number, and Fischer Hardness values can be determined in accordance with art-recognized methods. With some embodiments: refractive index values ($n_e^{20}$) and ABBE numbers are determined using a Metricon Model 2010 Prism Coupler, Thin Film Thickness/Refractive Index Measurement System, in accordance with the manufacturer's Operation and Maintenance Guide; and Fischer Hardness values are determined in accordance with ISO 14577 using a Fischer Technologies H100C Microhardness Measurement System.

Polymerizates prepared from the polymerizable compositions (the present invention can be used to form solid articles such as optical element(s) or device(s). As used herein the term "optical" means pertaining to or associated with light and/or vision. For example, the optical element or device can comprise ophthalmic elements and devices, display elements and devices, windows, mirrors, and/or active and passive liquid crystal cell elements and devices. As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as but not limited to bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors. As used herein the term "display" means the visible or machine-readable representation of information in words, numbers, symbols, designs or drawings. Non-limiting examples of display elements and devices include screens, monitors, and security elements, such as security marks. As used herein the term "window" means an aperture adapted to permit the transmission of radiation there-through. Non-limiting examples of windows include automotive and aircraft transparencies, filters, shutters, and optical switches. As used herein the term "mirror" means a surface that specularly reflects a large fraction of incident light.

The optical element or device previously mentioned can further comprise a polarizer, e.g., a linear polarizer, a circular polarizer or an elliptical polarizer. Suitable polarizers are know in the art. For example, the polarizer can be linearly polarizing and can be in the form of a coating, a film, or a wafer. A polarizing coating can include dichroic materials (including photochromic-dichroic materials) as described hereinbelow, and can be oriented in one or more directions as described below. Further, the polarizer may be in the form of a film which comprises a polymeric component and a dichroic material which is oriented in the direction in which the film is oriented. A polarizing wafer typically has a polarizer (either in the form of a polymeric film or a coating) sandwiched between two layers of transparent optical polymeric materials.

For example, the polarizer can comprise a polymeric component comprising poly(vinyl alcohol), polyvinyl butyral), polyethylene terephthalate, cellulose acetate butyrate, cellulose diacetate, cellulose triacetate, polyurethane, polyether, polyester, polyamide, polyalkyl(meth)acrylate, mixtures thereof and/or copolymers thereof.

Also, the polarizer can comprise a linearly polarizing film comprised of an optical film including a disperse phase of polymeric particles disposed within a continuous birefringent matrix which film can be oriented in one or more directions. The size and shape of the disperse phase particles, the volume fraction of the disperse phase, the film thickness and the amount of orientation are chosen to attain a desired degree of diffuse reflection and total transmission of radiation of a desired wavelength in the film. Such films and their preparation are described in U.S. Pat. No. 5,867,316 at column 6, line 47, to column 20, line 51, the cited portion of which is incorporated herein by reference. The polarizer, when linearly polarizing also can comprise the birefringent multilayer optical films described in U.S. Pat. No. 5,882,774, at column 2, line 63, to column 18, line 31, the cited portion of which is incorporated herein by reference. Further, polarizer also can comprise a two-component polarizer (i.e., dichroic and reflective polarizing components) such as that described in U.S. Pat. No. 6,096,375 at column 3, line 7 to column 19, line 46, the cited portion of which is incorporated herein by reference.

Additionally, the polarizer can be linearly polarizing and can comprise oriented film of polyvinyl alcohol, vinyl butyral, polyethylene terephthalate, polyalkyl(meth)acrylate, polyamide, poly(amide-ether) block copolymers, poly(ester-ether) block copolymers, poly(ether-urethane) block copolymers, poly(ester-urethane) block copolymers, and/or poly (ether-urea) block copolymers. The term "oriented film" as used in conjunction with a linearly polarizer, means that the film has at least a first general direction (of alignment) such that one or more other structures or components comprising the sheet are positioned or suitably arranged along that same general direction. For example, the alignment or ordering of a dichroic compound along the long-axis of the dichroic compound is essentially parallel to at least the first general direction of the film or layer. As used herein with reference to order or alignment of a material or structure, the term "general direction" refers to the predominant arrangement or orientation of the material, compound or structure. Further, it will be appreciated by those skilled in the art that a material, compound or structure can have a general direction even though there is some variation within the arrangement of the material, compound or structure, provided that the material, compound or structure has at least one predominate arrangement.

Suitable polarizers also can comprise a "K-type" polarizer in which the dichroic material(s) are prepared, for example, by dehydration of poly(vinylalcohol). Such polarizers often are referred to as inherent polarizers since the absorbing chromophore is the result of conjugation in the polymer backbone, rather than due to dichroic materials, dichroic dyes, being added to the polymeric component. Such K-type polarizers can comprise a film of oriented poly(vinyl alcohol) having light polarizing (dichroic) molecules comprised of conjugated blocks, such as poly(acetylene) blocks (i.e., —[CH=CH—]$_n$), formed by heating the oriented poly(vinyl alcohol) film in the presence of a dehydration catalyst such as vapor of aqueous hydrochloric acid. K-type polarizers also can be formed by affixing an acid donor layer comprising a photoacid generator to the film of oriented poly(vinyl alcohol), and exposing to radiant energy at a temperature sufficient to effect partial dehydration of the vinylalcohol polymer to a vinylalcohol/poly(acetylene)) copolymer. See, for example, U.S. Pat. No. 6,808,657.

As previously mentioned, the polarizer can comprise a dichroic material. Non-limiting examples of suitable dichroic materials can include, but are not limited to compounds such as azomethines, indigolds, thioindigoids, merocyanines, indans, quinophthalonic dyes, perylenes, phthaloperines, triphenodioxazines, indoloquinoxalines, imidazo-triazines, tetrazines, azo and (poly)azo dyes, benzoquinones, naphthoquinones, anthroquinone, (poly)anthroquinones, anthropyrimidinones, iodine, and/or iodates. As used herein the term 'compound' means a substance formed by the union of two or more elements, components, ingredients, or parts and includes, without limitation, molecules and macromolecules (for example polymers and oligomers) formed by the union of two or more elements, components, ingredients, or parts.

The dichroic material also can comprise a polymerizable dichroic compound. That is, the dichroic material can comprise at least one group that is capable of being polymerized (i.e., a "polymerizable group"). For example, although not limiting herein, in one non-limiting embodiment the dichroic compound can have at least one alkoxy, polyalkoxy, alkyl, or polyalkyl substituent terminated with at least one polymerizable group.

The dichroic material also can comprise a photochromic-dichroic compound. The term "photochromic-dichroic" means displaying both photochromic and dichroic (i.e., linearly polarizing) properties under certain conditions, which properties are at least detectable by instrumentation. Accordingly, "photochromic-dichroic compounds" are compounds displaying both photochromic and dichroic (i.e., linearly polarizing) properties under certain conditions, which properties are at least detectable by instrumentation. Thus, photochromic-dichroic compounds have an absorption spectrum for at least visible radiation that vanes in response to at least actinic radiation, and are capable of absorbing one of two orthogonal plane polarized components of at least transmitted radiation more strongly than the other (i.e., capable of exhibiting dichroism. Additionally, as with conventional photochromic compounds discussed hereinbelow, the photochromic-dichroic compounds disclosed herein can be thermally reversible. That is, the photochromic-dichroic compounds can switch from a first state to a second state in response to actinic radiation and revert back to the first state in response to thermal energy.

For example, according to various non-limiting embodiments disclosed herein, the photochromic-dichroic compound can have a first state having a first absorption spectrum, a second state having a second absorption spectrum that is different from the first absorption spectrum, and can be adapted to switch from the first state to the second state in response to at least actinic radiation and to revert back to the first state in response to thermal energy. Further, the photochromic-dichroic compound can be dichroic (i.e., linearly polarizing) in one or both of the first state and the second state. For example, although not required, the photochromic-dichroic compound can be linearly polarizing in an activated state and non-polarizing in the bleached or faded (i.e., not activated) state. As used herein, the term "activated state" refers to the photochromic-dichroic compound when exposed to sufficient actinic radiation to cause the at least a portion of the photochromic-dichroic compound to switch from a first state to a second state. Further, although not required, the photochromic-dichroic compound can be dichroic in both the first and second states. While not limiting herein, for example, the photochromic-dichroic compound can linearly polarize visible radiation in both the activated state and the bleached state. Further, the photochromic-dichroic compound can linearly polarize visible radiation in an activated state, and can linearly polarize UV radiation in the bleached state.

Examples of photochromic-dichroic compounds suitable for use in the present invention can include, but are not limited, to those described in detail in U.S. Patent Application Publication No. 2005/0012996A1 at paragraphs [0089] to [0339], which disclosure is incorporated herein by reference.

As previously mentioned, the polarizer can comprise an oriented polymeric film. The polymeric components and the dichroic material(s) (including dichroic photochromic materials as described above) used to prepare such polymeric film(s), and any other components which may be included, can be blended together and then subjected to any of a variety of processing techniques known in the art to form the film. Such techniques can include, for example, extrusion, solvent casting, calendering, blowing, molding, or combinations of such techniques. Alternatively, the composition used to prepare the polymeric component can be blended together and subjected to any of a variety of processing techniques known in the art to form the film. Once the film is formed, a solution comprising the dichroic material(s) can be incorporated into the film, such as by an imbibition process well know in the art, and the imbibed film then can be oriented to align the dichroic material(s).

The film can be fixed in the oriented configuration by any of a variety of fixing means known in the art. For example, a film oriented by stretching can be fixed in the oriented configuration to prevent recovery of the sheet to the pre-stretched configuration by mechanically fixing means (such as by the use of clamps). Other means can include thermofixing or thermal annealing, fixing the oriented film by heating. Where the film is prepared from reactive (e.g., crosslinkable) polymeric components, the film can be formed, such as by extrusion or solvent casting, in such a way that the components do not react. Once formed, the film can be oriented then fixed in the oriented configuration by reacting (e.g., crosslinking, including self-crosslinking) the polymeric components. For example, such crosslinking can be effectuated by subjecting the oriented film to conditions which promote the reaction of the functional groups of any reactive polymeric components, e.g., subjecting the oriented sheet to heat or radiation including actinic (ultraviolet) and/or ionizing (electron beam) radiation.

Additionally or alternatively, polymerizates prepared from the polymerizable compositions of the present invention can be used to prepare photochromic articles, including but not limited to, photochromic lenses. When used to prepare photochromic articles, such as photochromic lenses, the polymerizate should be transparent to that portion of the electromagnetic spectrum which activates the photochromic substance(s) incorporated in the matrix. More particularly, the polymerizate should be transparent to that wavelength of ultraviolet (UV) light that produces the colored or open form of the photochromic substance and that portion of the visible spectrum that includes the absorption maximum wavelength of the photochromic substance in its UV activated form (or open form). Photochromic substances that can be utilized with the polymerizates of the present invention include, but are not limited to, organic photochromic compounds or substances containing same that can be either: (a) incorporated (e.g., dissolved, dispersed or diffused) into such polymerizates; or (b) added to the polymerizable composition prior to polymerization.

The present invention also relates to photochromic articles that include: (a) a polymerizate of one or more polymerizable compositions of the present invention; and (b) a photochromic amount of an organic photochromic material.

Examples of classes of organic photochromic materials that can be included in the photochromic articles of the present invention include, but are not limited to, spiro(indoline)naphthoxazines, spiro(indoline)benzoxazines, benzopyrans, naphthopyrans, chromenes, organo-metal dithizonates, fulgides and fulgimides and mixtures or combinations of two or more thereof.

A first group of organic photochromic substances contemplated for use to form the photochromic articles of the present invention are those having an activated absorption maximum within the visible range of greater than 590 nanometers, e.g., between greater than 590 to 700 nanometers. These materials typically exhibit a blue, bluish-green, or bluish-purple color when exposed to ultraviolet light in an appropriate solvent or matrix. Examples of classes of such substances that are useful in the present invention include, but are not limited to, spiro (indoline)naphthoxazines and spiro(indoline)benzoxazines. These and other classes of such photochromic substances are described in the open literature. See for example, U.S. Pat. Nos. 3,562,172; 3,578,602; 4,215,010; 4,342,668; 5,405,958; 4,637,698; 4,931,219; 4,816,584; 4,880,667; 4,818,096. See also, for example: Japanese Patent Publication 62/195383; and the text, Techniques in Chemistry, Volume III, "Photochromism," Chapter 3, Glenn H. Brown, Editor, John Wiley and Sons, Inc., New York, 1971.

A second group of organic photochromic substances contemplated for use to form the photochromic articles of the present invention are those having at least one absorption maximum and preferably two absorption maxima, within the visible range of between 400 and less than 500 nanometers. These materials typically exhibit a yellow-orange color when exposed to ultraviolet light in an appropriate solvent or matrix. Such compounds include certain chromenes, such as benzopyrans and naphthopyrans. Examples of such chromenes are described in the following non-limiting list of U.S. Pat. Nos. 3,567,605; 4,826,977; 5,066,818; 4,826,977; 5,066,818; 5,466,398; 5,384,077; 5,238,931; and 5,274,132.

A third group of organic photochromic substances contemplated for use to form the photochromic articles of the present invention are those having an absorption maximum within the visible range of between 400 to 500 nanometers and another absorption maximum within the visible range of between 500 to 700 nanometers. These materials typically exhibit color(s) ranging from yellow/brown to purple/gray when exposed to ultraviolet light in an appropriate solvent or matrix. Examples of these substances include, but are not limited to, certain benzopyran compounds, having substituents at the 2-position of the pyran ring and a substituted or unsubstituted heterocyclic ring, such as a benzothieno or benzofurano ring fused to the benzene portion of the benzopyran. Such materials are described in U.S. Pat. No. 5,429,774.

Other photochromic substances contemplated are photochromic organo-metal dithizonates, such as (arylazo)-thioformic arylhydrazidates, including, for example, mercury dithizonates, which are described in, for example, U.S. Pat. No. 3,361,706. Fulgides and fulgimides, such as 3-furyl and 3-thienyl fulgides and fulgimides, are described in U.S. Pat. No. 4,931,220 at column 20, line 5 through column 21, line 38.

The disclosures relating to such photochromic substances in the above described patents are incorporated herein by reference in each case in their entirety. The photochromic articles of the present invention can contain one photochromic substance or a mixture of two or more photochromic substances, as desired. Mixtures of photochromic substances can be used to attain certain activated colors such as, but not limited to, a near neutral gray or brown.

Each of the photochromic substances described herein can be used in amounts and in ratios (when mixtures are used) such that a polymerizate to which the mixture of compounds is applied or in which they are incorporated exhibits a desired resultant color, such as a substantially neutral color, such as shades of gray or brown when activated with unfiltered sunlight. With some embodiments, a near neutral or neutral color can be obtained with the colors of the activated photochromic substances. The relative amounts of the aforesaid photochromic substances used can vary and depend in part upon the relative intensities of the color of the activated species of such compounds, and the ultimate color desired.

The photochromic compounds or substances described herein can be applied to or incorporated into the polymerizate by various methods described in the art. Such methods include, but are not limited to, dissolving or dispersing the substance within the polymerizate, such as: imbibition of the photochromic substance into the polymerizate by immersion of the polymerizate in a hot solution of the photochromic substance or by thermal transfer; providing the photochromic substance as a separate layer between adjacent layers of the polymerizate, such as a part of a polymer film or polymer layer; and applying the photochromic substance as part of a coating or polymer layer placed on the surface of the polymerizate. The term "imbibition" or "imbibe" means permeation of the photochromic substance or substances alone into the polymerizate, solvent assisted transfer absorption of the photochromic substance(s) into a porous polymer, vapor phase transfer, and other such transfer mechanisms.

The amount of photochromic substance(s) or composition containing photochromic substance(s) applied to or incorporated into the polymerizate is not critical provided that a sufficient amount is used to produce a photochromic effect discernible to the naked eye upon activation. Generally, such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity. With some embodiments, the amount of total photochromic substance incorporated into or applied to a photochromic optical polymerizate can range from 0.15 to 0.35 milligrams per square centimeter of surface to which the photochromic substance(s) is incorporated or applied.

It is also contemplated that photochromic substances can be added to the polymerizable compositions of the present invention prior to curing. When this is done, however, it is preferred that the photochromic substance(s) be resistant to potentially adverse interactions with initiator(s) that can be present and/or the sulfide linkages within the monomers that form the polymerizate. Such adverse interactions can result in deactivation of the photochromic substance(s), such as by trapping them in either an open or closed form. Organic photochromic substances sufficiently encapsulated within a matrix of an organic polymerizate, as described in U.S. Pat. No. 4,931,220, can also be incorporated into the polymerizable compositions of the present invention prior to curing.

EXAMPLES

The present invention is more particularly described in the following examples, which are intended to be illustrative only, since numerous modifications and variations therein will be apparent to those skilled in the art. Unless otherwise specified, all parts and percentages are by weight.

Example 1

Synthesis of Formula (Ib)

Step 1

The materials listed below were charged to a 500 mL round bottom flask that was equipped with a reflux condenser, a magnetic stirrer, and an oil heating bath, and the mixture was stirred at 100° C. for 1 hour,

| Material | Weight, grams | Number of Moles |
|---|---|---|
| DMDS[1] | 50.00 g | 0.32 |
| Ethylene carbonate | 62.00 g | 0.70 |
| Potassium carbonate | 2.34 | 0.017 |
| Dimethylformamide | 50.0 | — |

[1]Dimercaptodiethylsulfide

Frothing of the reaction mixture occurred due to the evolution of carbon dioxide gas formed during the reaction. The resulting product mixture was cooled to room temperature and poured into 100 mL of water, with agitation. The resulting precipitated product was isolated by suction filtration, washed with ethanol and ethyl acetate, and dried in a vacuum chamber at ambient room temperature. Nuclear magnetic resonance (NMR) spectra showed the product to have a structure consistent with the following chemical formula:

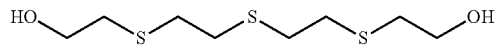

Step 2

The materials listed below were charged to a 500 mL 4-neck round bottom flask that was equipped with a thermometer, a reflux condenser, a mechanical stirrer, an air inlet/bubbling tube, and an oil heating bath, and the mixture was heated to reflux while being sparged with air.

| Material | Weight, grams | Number of Moles |
|---|---|---|
| Product Step 1 | 45.00 g | 0.186 |
| Methyl methacrylate | 106.00 g | 1.06 |
| Cesium carbonate | 0.88 | 0.0027 |
| 4-Methoxyphenol (MEHQ) | 0.88 | 0.0071 |
| Heptanes | 120 | — |

Fractions of distillate were collected periodically, and analyzed by gas chromatography in order to monitor the generation of methanol from the reaction. Additional heptane solvent was added periodically in order to maintain the reaction mixture at an approximately constant volume. After a reaction time of approximately 4 hours at 85-97° C., methanol was no longer being generated, and the reaction mixture was cooled to room temperature, and washed three times with 50 mL of 10 weight percent aqueous sodium hydroxide solution in order to remove excess MEHQ. Activated carbon (2 grams) was added, followed by stirring at room temperature for 1 hour, filtration, and concentration under vacuum on a rotary evaporator. NMR spectra showed the product to have a structure consistent with the following chemical formula:

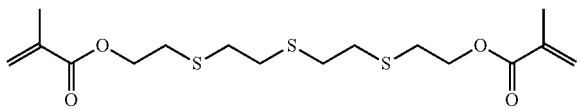 [SMILES: C=C(C)C(=O)OCCSCCSCCSCCOC(=O)C(=C)C]

Example 2

Synthesis of a Mixture of Formula (Ib)+Formula (I), where p=1, $R^1$=$CH_3$, $R^2$=—$CH_2$—$CH_2$—S—$CH_2$—$CH_2$—, $R^3$=—$CH_2$—$CH_2$—, $R^6$=$CH_3$, and $R^7$=$CH_3$ Step 1

The materials listed below were charged to a 200 mL round bottom flask that was equipped with a water cooled condenser and a magnetic stirrer, and mixed at ambient room temperature for approximately 120 hours.

| Material | Weight, grams | Number of Moles |
|---|---|---|
| DMDS[1] | 61.6 g | 0.40 |
| 2,2-dimethoxypropane | 10.4 g | 0.10 |
| p-TSA[2] | 0.05 | 0.00026 |

[2]p-toluenesulfonic acid

Residual volatiles were removed from the resulting product mixture by vacuum stripping with a rotary evaporator. NMR spectra showed the products to have structures consistent with the following chemical formulas in the proportions indicated:

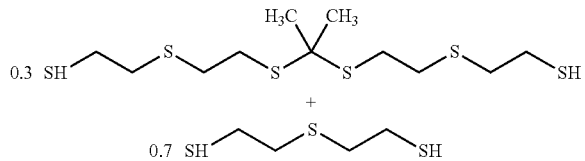

Step 2

The materials listed below were charged to a 500 mL round bottom flask that was equipped with a reflux condenser, a magnetic stirrer, and an oil heating bath, and the mixture was stirred at 100° C. for 1 hour.

| Material | Weight, grams | Number of Moles |
|---|---|---|
| Product Mixture of Step 1 | 50.00 g | 0.23[3] |
| Ethylene carbonate | 44.27 g | 0.50 |
| Potassium carbonate | 1.72 | 0.012 |
| Dimethylformamide | 50.0 | — |

[3]Based on average molecular weight of 218.

Frothing of the reaction mixture occurred due to the evolution of carbon dioxide gas formed during the reaction. The resulting product mixture was cooled to room temperature, and poured into 100 mL of water with agitation. The resulting precipitate was isolated by suction filtration, washed with ethanol and ethyl acetate, and dried in a vacuum chamber at ambient room temperature. NMR spectra showed the products to have structures consistent with the following chemical formulas in the proportions indicated:

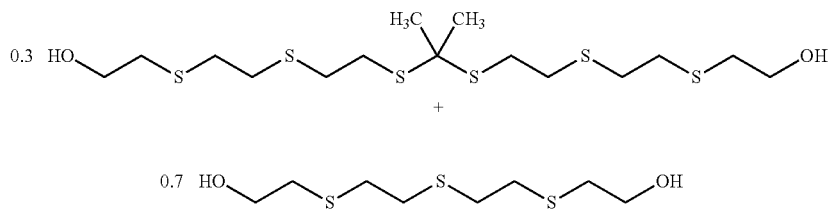

Step 3

The materials listed below were charged to a 500 mL 4-neck round bottom flask that was equipped with a thermometer, a reflux condenser, a mechanical stirrer, an air inlet/bubbling tube, and an oil heating bath, and the mixture was heated to reflux while being sparged with air,

| Material | Weight, grams | Number of Moles |
|---|---|---|
| Product of Step 2 | 42.53 g | 0.14[4] |
| Methyl methacrylate | 83.93 g | 0.84 |
| Cesium carbonate | 0.72 | 0.0022 |
| 4-Methoxyphenol (MEHQ) | 0.72 | 0.0058 |
| Heptanes | 120 | — |

[4]Based on average molecular weight of 306.

Fractions of distillate were collected and analyzed by gas chromatography in order to monitor the generation of methanol from the reaction. Additional heptane solvent was added periodically in order to maintain the reaction mixture at an approximately constant volume. After a reaction time of approximately 4 hours at 85-87° C., methanol was no longer being generated, and the reaction mixture was cooled to room temperature, and washed three times with 50 mL of 10 weight percent aqueous sodium hydroxide solution in order to remove excess MEHQ. Activated carbon (2 grams) was added, followed by stirring at room temperature for 1 hour, filtration, and concentration under vacuum on a rotary evaporator. NMR spectra showed the products to have structures consistent with the following chemical formulas in the proportions indicated:

Polymer Casting Procedure for Examples 1 and 2

The materials listed below were mixed with a magnetic stirring bar at 30-35° C., for 1 hour, and then injected into a two-part flat glass mold with a cavity thickness of 1 mm, and cured in a forced air oven using Cure Cycle #1 in Table 1 shown below. The polymer properties of the resulting clear polymer sheets are listed in the Table 2 table below,

| Material | Example 1A Weight, grams | Example 2A Weight, grams |
|---|---|---|
| Product of Example 1 | 7.39 | — |
| Product of Example 2 | — | 7.39 |
| γ-Terpinene | 0.11 | 0.11 |
| Luperox 256 ® peroxide[5] | 0.165 | 0.165 |

[5]Reported to be 2,5-dimethyl-2,5-di(2-ethylhexanoylperoxy) hexane from Arkema Inc.

TABLE 1

| | Cure Cycle #1 | | |
|---|---|---|---|
| Step # | Duration of Step (hours) | Cumulative Time (hours) | Final Temperature (° C.) |
| 1 (initial temp.) | 0 | 0 | 71 |
| 2 | 8 | 8 | 77 |
| 3 | 2 | 10 | 79 |
| 4 | 2 | 12 | 82 |
| 5 | 3 | 15 | 95 |
| 6 | 1 | 16 | 95 |
| 7 | 2 | 18 | 85 |

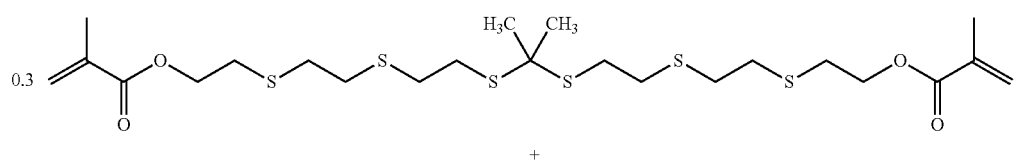

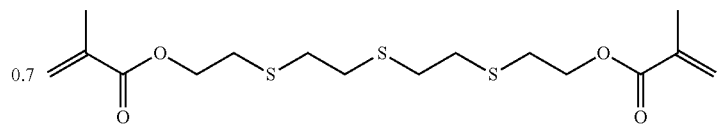

TABLE 2

Polymer Properties

| Property | Example 1A | Example 2A |
|---|---|---|
| Fischer Microhardness, N/mm$^2$[6] | 94 | 89 |
| Refractive index, $n_e^{20}$[7] | 1.586 | 1.5919 |
| Abbe Number[7] | 44 | 43 |
| Yellowness index (1 mm thickness)[8] | 0.7 | 0.5 |

[6] Fischer microhardness was tested according to ISO 14577-07 and was measured using a FISCHERSCOPE ® H-100SMC available from Fischer Technology, Inc. The Fischer microhardness (FMH) of the polymerizates, ±3 Newtons/mm$^2$, was measured at a load of 300 milliNewton (mN), following a load application of 0-300 mN in 15 seconds. The results are an arithmetic average of 5 measurements.
[7] The refractive index and Abbe Number were measured at 546 nm (mercury e-line) and 23° C, using a METRICON ® Model 2010M prism coupler according to ASTM C1648-06.
[8] The yellowness index was measured using a HunterLab ULTRASCAN ® PRO according to ASTM E313-10. The path length for the samples was equal to the sample thickness.

Polymer Casting of Example 1 with Different Polymerization Moderators

The materials listed in Tables 3 and 4 below were mixed with a magnetic stirring bar at approximately 25° C., for 1 hour and injected into a two-part flat glass mold with a cavity thickness of 3 mm. Examples 1B through 1M in Tables 3 and 4 were cured in a forced air oven using Cure Cycle #2 in Table 5 shown below; and Examples 1N to 1R in Table 6 were cured in the same fashion except using Cure Cycle 3 in Table 7. The polymer properties of the resulting clear polymer sheets of Examples 1B to 1L and Comparative Example 1 (CE-1) are listed in Tables 3 and 4 below and those of Examples 1N to 1R are in Table 6.

TABLE 3

Examples 1B through 1G

| | CE-1 | 1B | 1C | 1D | 1E | 1F | 1G | 1H |
|---|---|---|---|---|---|---|---|---|
| Product of Example 1, grams | 18.75 | 18.47 | 18.47 | 18.47 | 18.65 | 18.56 | 18.47 | 18.47 |
| Styrene, grams | 6.25 | 6.155 | 6.155 | 6.155 | 6.22 | 6.19 | 6.155 | 6.155 |
| γ-Terpinene, grams | — | 0.375 | — | — | — | — | — | — |
| α-Terpinene, grams | — | — | 0.375 | — | — | — | — | — |
| Terpinolene, grams | — | — | — | 0.375 | — | — | — | — |
| 2,6-Dimethyl-2,6-Octatriene, grams | — | — | — | — | 0.125 | 0.25 | 0.375 | — |
| α-Methyl-styrene dimer, grams | — | — | — | — | — | — | — | 0.375 |
| Luperox 256 ® peroxide[5], grams | 0.55 | 0.55 | 0.55 | 0.55 | 0.55 | 0.55 | 0.55 | 0.55 |
| Polymer Fischer Microhardness N/mm$^2$[6] | 117 | 114 | 109 | 110 | 112 | 114 | 116 | 116 |
| Refractive Index, $n_e^{20}$[7] | 1.590 | 1.589 | 1.588 | 1.589 | 1.589 | 1.590 | 1.589 | 1.590 |
| Yellowness Index[8] | 2.3 | 1.2 | 1.0 | 1.5 | 1.3 | 2.4 | 2.6 | 1.8 |
| Uncontrolled polymerization[9] | Yes | No | No | No | No | No | No | No |
| Cracked[10] | Yes | No | No | No | No | No | No | No |
| Pre-released[11] | Yes | No | No | No | No | Slight | Yes | No |

[9] A process subject to erratic and/or excessive rates of polymerization, leading to severe striation, and/or significant surface irregularities, and/or severely fractured or broken sample.
[10] Refers to the polymer sample (sheet or lens) having fissures and/or being broken.
[11] Refers to pre-mature separation of the polymer sheet or lens tested below from the glass mold during the cure cycle, resulting in a surface defect.

TABLE 4

Examples 1I through 1M

| | 1I | 1J | 1K | 1L | 1M |
|---|---|---|---|---|---|
| Product of Example 1, grams | 18.47 | 18.47 | 18.47 | 13.544 | 13.544 |
| Styrene, grams | 6.155 | 6.155 | 6.155 | 11.081 | 11.081 |
| γ-Terpinene, grams | — | — | — | 0.375 | — |
| α-Methyl-styrene dimer, grams | — | — | — | — | 0.375 |
| Dipentene, grams | 0.375 | — | — | — | — |
| Triphenylmethane, grams | — | 0.375 | — | — | — |
| 3-Carene, grams | — | — | 0.375 | — | — |
| Luperox 256 ® peroxide[5], grams | 0.55 | 0.55 | 0.55 | 0.55 | 0.55 |
| Polymer Fischer Microhardness, N/mm$^2$[6] | — | — | — | 121 | 126 |
| Refractive Index, $n_e^{20}$[7] | — | — | — | 1.593 | 1.593 |
| Yellowness index[8] | — | — | — | NA | 1.3 |
| Uncontrolled polymerization[9] | No | No | No | No | No |
| Cracked[10] | Yes | Yes | Yes | No | No |
| Pre-released[11] | Yes | Yes | Yes | No | No |

TABLE 5

Cure Cycle #2

| Step # | Duration of Step (hours) | Cumulative Time (hours) | Final Temperature (° C.) |
|---|---|---|---|
| 1 | 3 | 3 | 55 |
| 2 | 3 | 6 | 71 |

TABLE 5-continued

Cure Cycle #2

| Step # | Duration of Step (hours) | Cumulative Time (hours) | Final Temperature (° C.) |
|---|---|---|---|
| 3 | 8 | 14 | 77 |
| 4 | 2 | 16 | 79 |
| 5 | 2 | 18 | 82 |
| 6 | 3 | 21 | 95 |
| 7 | 1 | 22 | 95 |
| 8 | 2 | 24 | 85 |

TABLE 6

Examples 1N through 1R

| | 1N | 1O | 1P | 1Q | 1R |
|---|---|---|---|---|---|
| Product of Example 1, grams | 18.47 | 18.56 | 18.655 | 18.47 | 13.544 |
| Styrene, grams | 6.155 | 6.19 | 6.22 | 6.155 | 11.081 |
| γ-Terpinene, grams | 0.375 | 0.25 | 0.125 | — | — |
| α-Methyl-styrene dimer, grams | — | — | — | 0.375 | 0.375 |
| Luperox 256 ® peroxide[12], grams | 0.125 | 0.125 | 0.125 | 0.125 | 0.125 |
| Polymer Fischer Microhardness, $N/mm^{2[6]}$ | 118 | 120 | 120 | 120 | 129 |
| Refractive Index, $n_e^{20[7]}$ | 1.591 | 1.591 | 1.591 | 1.593 | 1.594 |
| Yellowness index[8] | 1.4 | 1.3 | 1.5 | NA | 1.4 |
| Uncontrolled polymerization[9] | No | No | No | No | No |
| Cracked[10] | No | No | No | No | No |
| Pre-released[11] | No | No | No | No | No |

[12]Reported to be 1,1-di(tert-butylperoxy)-3,3,5-trimethylcyclohexane from Arkema Inc.

TABLE 7

Cure Cycle #3

| Step # | Duration of Step (hours) | Cumulative Time (hours) | Final Temperature (° C.) |
|---|---|---|---|
| 1 | 3 | 3 | 65 |
| 2 | 9 | 12 | 88 |
| 3 | 3 | 15 | 122 |
| 4 | 1 | 16 | 122 |
| 5 | 2.5 | 18.5 | 85 |

Polymer Lens Casting of Example 1

The materials listed in Tables 8 and 10 below were mixed with a magnetic stirring bar at 20-25° C. for 1 hour and injected into a (−7) diopter finished single vision (FSV) 83 mm diameter lens mold constructed from a front circular glass mold (1.5) diopter curvature and a back circular glass mold (−9) diopter curvature, a spacer gasket made of ethylene/propylene/diene monomer rubber, and a metal spring clamp. The final cast lenses had a center thickness of 2.0 mm, edge thickness 14 mm, and diameter 75 mm. Examples 1S through 1U in Table 8 were cured in a forced air oven using Cure Cycle #4 in Table 9 shown below; and Examples 1V and 1W in Table 10 were cured in the same fashion except using Cure Cycle #5 in Table 11. The number of the (−7) diopter lenses cast as well as the percentage of those that were pre-released are included in these tables,

TABLE 8

Examples 1S through 1U

| | Example 1S | Example 1T | Example 1U |
|---|---|---|---|
| Product of Example 1, grams | 877.5 | 855 | 840 |
| Styrene | 600 | 600 | 600 |
| Maleic Anhydride | 0 | 22.5 | 37.5 |
| γ-Terpinene, grams | 22.5 | 22.5 | 22.5 |
| Luperox 256 ® peroxide[5], grams | 11.25 | 11.25 | 11.25 |
| Number of -7 FSV lenses cast | 21 | 21 | 21 |
| Percentage lenses pre-released[11] | 62% | 19% | 5% |

TABLE 9

Cure Cycle #4

| Step # | Duration of Step (hours) | Cumulative Time (hours) | Final Tempeaure (° C.) |
|---|---|---|---|
| 1 | 0 | 0 | 40 |
| 2 | 6 | 6 | 42 |
| 3 | 5 | 11 | 46 |
| 4 | 4 | 15 | 50 |
| 5 | 4 | 19 | 55 |
| 6 | 1 | 20 | 57 |
| 7 | 2 | 22 | 63 |
| 8 | 3 | 25 | 75 |
| 9 | 3 | 28 | 75 |

TABLE 10

Examples 1V and 1W

| | Exam 1V | Example 1W |
|---|---|---|
| Product of Example 1, grams | 292.5 | 282.5 |
| Styrene | 200 | 200 |
| Maleic Anhydride | 0 | 10 |
| γ-Terpinene, grams | 7.5 | 7.5 |
| Luperox 256 ® peroxide[5], grams | 3.75 | 3.75 |
| Number of -7 FSV lenses cast | 7 | 7 |
| Percentage of lenses pre-released[11] | 57% | 0% |

TABLE 11

Cure Cycle #5

| Step # | Duration of Step (hours) | Cumulative Time (hours) | Final Temperature (° C.) |
|---|---|---|---|
| 1 | 6 | 6 | 40 |
| 2 | 12 | 18 | 55 |
| 3 | 3 | 21 | 75 |
| 4 | 3 | 24 | 75 |

Example 3

Synthesis of Formula IV

Step 1

Potassium carbonate (8.06 g, 0.06 mole eq.) was added to a solution of a 2/1 (mol/mol) adduct (396.91 g, 2.12 mole eq. by thiol) of dimercaptodiethylsuifide (DMDS) and propargyl alcohol (PA) prepared according to the procedure of Example 1 of U.S. Pat. No. 7,553,925 B2, which disclosure is incorporated herein by reference, and dimethylformamide (250 mL) in a 1000-mL round bottom flask equipped with a magnetic stir bar and fitted with a temperature probe, reflux condenser and nitrogen inlet. Ethylene carbonate (207.17 g, 2.35 mole eq.) was subsequently added to the mixture. The reaction flask was set in an oil bath for heating on a hotplate. The reaction mixture was gradually heated to 90° C. over the course of several hours. The reaction was evidenced by bubbling as a result of the evolution of carbon dioxide gas. Once the bubbling stopped, the reaction mixture was allowed to cool. This mixture was gradually added to ice-water under agitation, forming a precipitate. This precipitate was filtered and washed multiple times with water. Upon final filtration and drying, 493 g of a tannish colored solid was obtained. The resulting triol was characterized as having a hydroxyl number of 344 mg/g (theoretical 364 mg/g), Step 2

The product of Step 1 (362.02 g, 2.13 mole eq.), triethylamine (258.74 g, 2.56 mole eq.), and tetrahydrofuran (550 mL) were added to a 2000 mL round bottom flask equipped with a stirrer, addition funnel, and nitrogen inlet. The resulting solution was cooled to 6° C., and methacryloyl chloride (245 g, 2.34 mole eq.) was added dropwise via an addition funnel. The addition rate was maintained so that the reaction temperature did not exceed 10° C. Upon completion of the addition, the reaction mixture was allowed to come to ambient temperature. The reaction mixture was filtered to provide a liquid, which was later dissolved in methylene chloride. The resulting solution was washed using 5 weight percent HCl, 10 weight percent NaHCO$_3$, and water until a neutral pH was achieved. The solution was dried over MgSO$_4$, and solvent was removed under reduced pressure to provide 403 g of liquid product. No residual hydroxyl groups were determined by analysis.

Polymer Casting Procedure for Example 3

Polymers prepared with Example 3 were based on the following casting composition: 98.5 weight percent monomer; 1.5 weight percent γ-terpinene; and 2.2 parts per hundred (phr) Luperox 256® peroxide[5]. The monomer compositions are listed below in Table 12. The components were charged to a vessel and mixed until a homogeneous mixture was obtained. The mixture was briefly held under reduced pressure, and then injected into a two-part flat glass mold with a cavity thickness of 3.2 mm. The filled mold was subjected to heating in a forced air oven using a pre-determined curing cycles #6 or #7 listed in Tables 14 and 15. Upon completion of the cure cycle, the mold was allowed to cool and the polymer was released from the mold. The resulting polymer properties are summarized in Table 13.

TABLE 12

Monomer Compositions in Weight Percent

| Example | Example 3 | Styrene | SR-368D[13] |
|---|---|---|---|
| 3A | 100 | | |
| 3B | 70 | 30 | |
| 3C | 60 | 40 | |
| 3D | 66 | 29 | 5 |

[13]Reported to be tris(2-hydroxyethyl)isocyanurate triacrylate from Sartomer Company, Inc.

TABLE 13

Casting Summary

| Example | Cure cycle # | FMH (N/mm$^2$)[6] | RI (e-line)[7] | Abbe number[7] |
|---|---|---|---|---|
| 3A | 6 | 37 | 1.604 | 40 |
| 3B | 7 | 75 | 1.597 | 37 |
| 3C | 7 | 83 | 1.594 | 36 |
| 3D | 7 | 112 | 1.595 | 38 |

TABLE 14

Cure Cycle #6

| Step # | Duration of Step (hours) | Cumulative Time (hours) | Final Temperature (° C.) |
|---|---|---|---|
| 1 | 0 | 0 | 71 |
| 2 | 8 | 8 | 77 |
| 3 | 2 | 10 | 79 |
| 4 | 2 | 12 | 82 |
| 5 | 3 | 15 | 95 |
| 6 | 1 | 16 | 95 |
| 7 | 2 | 18 | 85 |

TABLE 15

Cure Cycle #7

| Step # | Duration of Step (hours) | Cumulative Time (hours) | Final Temperature (° C.) |
|---|---|---|---|
| 1 | 3 | 3 | 55 |
| 2 | 3 | 6 | 71 |
| 3 | 8 | 4 | 77 |
| 4 | 2 | 16 | 79 |
| 5 | 2 | 18 | 82 |
| 6 | 3 | 21 | 95 |
| 7 | 1 | 22 | 95 |
| 8 | 2 | 24 | 85 |

Synthesis of Co-Monomer A of Formula (IIb)

Bis-[(2-methacryloylthio)ethyl]sulfide Formula (IIb), where $R^6=CH_3$) was synthesized from DMDS and methacryloyl chloride, according to the procedure given in the following reference: Tatsuhito Matsuda, Yasuaki Funae, Masahiro Yoshida, and Tetsuya Yamamoto, "Novel Bifunctional Thiolcarboxylic Acid Esters Useful as Crosslinking Agents for Optical Materials," *Synthetic Communications*, 30 (16), pp. 3041-3045 (2000), which disclosure is incorporated herein by reference.

Synthesis of Co-Monomer B of Formula III, where $L^4=-CH_2-CH_2-S-CH_2-CH_2-$, $L^5=-CH_2-CH_2-$, $R^9=CH_3$, $R^{10}=CH_3$, and u 2

The amounts of ethylene glycol dimethacrylate and DMDS listed in the table below were mixed together in a glass bottle, using a magnetic stirrer, for approximately 30 minutes at 20-25° C. The TOP catalyst (trioctylphosphine) was then added, whereupon the mixture became hot due to an exothermic reaction. The resulting mixture was stirred with a magnetic stirrer for approximately 2 hours. Analysis by Iodometric titration revealed that all of the SH groups of the DMDS had been reacted.

| Ingredients | Amount, grams |
|---|---|
| Ethylene glycol dimethacrylate | 72.00 |
| DMDS[(1)] | 28.00 |
| TOP | 0.05 |

Casting of Various Mixtures of Example 1 and Co-Monomers A and B to Produce Examples 4 to 9 and CE-2

The materials listed in Table 16 below were mixed with a magnetic stirring bar at 30-35° C., for 1 hour, and injected into a two-part flat glass mold with a cavity thickness of 32 mm, and cured in a forced air oven using Cure Cycle #8 in Table 17 shown below. The polymer properties of the resulting clear polymer sheets are listed in Table 16,

TABLE 16

Examples 4 through 9 and CE-2

| | CE-2 | Example 4 | Example 5 | Example 6 | Example 7 | Example 8 | Example 9 |
|---|---|---|---|---|---|---|---|
| Product of Example 1, grams | — | 17.24 | 17.73 | — | — | — | 9.85 |
| Co-monomer A, grams | 19.7 | 7.39 | — | 17.73 | 15.7 | 17.24 | 5.91 |
| Co-monomer B, grams | — | — | 1.97 | 1.97 | 4.00 | 7.39 | 3.94 |
| γ-Terpinene, grams | 0.30 | 6.40 | 0.298 | 0.298 | 0.30 | 0.40 | 0.298 |
| Luperox 256 ® peroxide[(5)], grams | 0.44 | 0.55 | 0.44 | 0.44 | 0.44 | 0.55 | 0.44 |
| Fischer Microhardness, N/mm$^2$[(6)] | 150 | 96 | 92 | 119 | 105 | 79 | 75 |
| Refractive Index, $n_e^{20}$[(7)] | 1.6269 | 1.5980 | 1.5819 | 1.6199 | 1.6125 | 1.6029 | 1.5916 |
| Abbe Number[(7)] | 36 | 40 | 45 | 36 | 37 | 38 | 40 |
| Yellowness Index[(8)] | 1.6 | 2.0 | 1.5 | 2.1 | 1.1 | 1.2 | 1.4 |

TABLE 17

Cure Cycle #8

| Step # | Duration of Step (hours) | Cumulative Time (hours) | Final Temperature (° C.) |
|---|---|---|---|
| 1 | 6 | 6 | 40 |
| 2 | 6 | 12 | 68 |
| 3 | 3 | 15 | 95 |
| 4 | 1 | 16 | 95 |
| 8 | 2 | 18 | 85 |

The present invention has been described with reference to specific details of particular embodiments thereof. It is not intended that such details be regarded as limitations upon the scope of the invention except insofar as and to the extent that they are included in the accompanying claims.

We claim:

1. A polymerizable composition comprising:
(a) at least one first (meth)acrylate functional monomer represented by the following Formula (I),

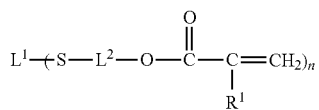

wherein,
$L^1$ is selected from:
a divalent linking group represented by the following Formula (A),

wherein Y is O or S,
multivalent linear or branched optionally substituted $C_1$-$C_{25}$ alkyl,
multivalent optionally substituted $C_3$-$C_{12}$ cycloalkyl, and combinations thereof, optionally interrupted with at least one of —S—, —O—, and combinations thereof,
$L^2$ is independently for each n a divalent optionally substituted hydrocarbyl group optionally interrupted with at least one of —O— and —S—,
$R^1$ is independently selected for each n from hydrogen and methyl, and n is from 2 to 6;
(b) at least one second (meth)acrylate functional monomer represented by the following Formula (III),

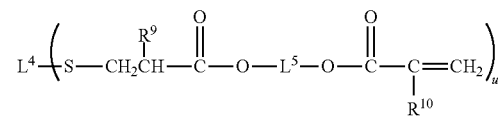

wherein,
$L^4$ is a multivalent optionally substituted hydrocarbyl group optionally interrupted with at least one of —C(O)—, —S—, —O— and combinations thereof,
$L^5$ is independently for each u a divalent optionally substituted hydrocarbyl group,
$R^9$ and $R^{10}$ are each independently selected for each u from hydrogen and methyl,
and
u is from 2 to 6;
(c) optionally, a polymerization moderator; and
(d) optionally, at least one monoethylenically unsaturated monomer.

2. The polymerizable composition of claim 1 wherein, $L^2$ is independently for each n selected from divalent optionally substituted linear or branched $C_1$-$C_{25}$ alkyl, divalent optionally substituted $C_3$-$C_{12}$ cycloalkyl, divalent optionally substituted aryl, and combinations thereof optionally interrupted with at least one of —O— and —S—.

3. The polymerizable composition of c a wherein,
L$^1$ is selected from multivalent linear or branched C$_1$-C$_{10}$ alkyl optionally interrupted with at least one of —S—, —O— and combinations thereof, and
L$^2$ is independently for each n selected from divalent linear or branched C$_1$-C$_{10}$ alkyl optionally interrupted with at least one —O—.

4. The polymerizable composition of claim 3 wherein,
L$^1$ is selected from multivalent linear or branched C$_1$-C$_{10}$ alkyl interrupted with at least one —S— group, and
n is 2 or 3.

5. The polymerizable composition of claim 1 wherein,
n is 2, and
L$^1$ is represented by the following Formula (B),

—(R$^2$—S)$_p$—R$^3$  (B)

wherein,
R$^2$ for each p is independently selected from linear or branched optionally substituted C$_1$-C$_{10}$ alkyl, and optionally substituted C$_3$-C$_{12}$ cycloalkyl,
R$^3$ is selected from linear or branched optionally substituted C$_1$-C$_{10}$ alkyl, and optionally substituted C$_3$-C$_{12}$ cycloalkyl, and
p is 0 to 10.

6. The polymerizable composition of claim 5 wherein,
L$^2$ is represented by the following Formula (C), —(R$^4$—O)$_q$—R$^5$—  (C)

wherein,
R$^4$ for each p is independently selected from linear or branched optionally substituted C$_1$-C$_{10}$ alkyl, and optionally substituted C$_3$-C$_{12}$ cycloalkyl,
R$^5$ is selected from linear or branched optionally substituted C$_1$-C$_{10}$ alkyl, and optionally substituted C$_3$-C$_{12}$ cycloalkyl, and
q is 0 to 10.

7. The polymerizable composition of claim 1 wherein,
n is 2,
L$^1$ is selected from,
(i) a divalent linking group represented by the following Formula (D),

—C(R$^6$)(R$^7$)—  (D)

wherein
R$^6$ and R$^7$ are each independently selected from hydrogen, linear or branched optionally substituted C$_1$-C$_{10}$ alkyl, and optionally substituted C$_3$-C$_{12}$ cycloalkyl, or R$^6$ and R$^7$ together form a C$_4$-C$_{12}$ optionally substituted cycloalkyl,
and
(ii) the divalent linking group represented by Formula (A), and
L$^2$ is represented by the following Formula (B), —(R$^2$—S)$_p$—R$^3$—  (B)

wherein,
R$^2$ for each p is independently selected from linear or branched optionally substituted
C$_1$-C$_{10}$ alkyl, and optionally substituted C$_3$-C$_{12}$ cycloalkyl,
R$^3$ is selected from linear or branched optionally substituted C$_1$-C$_{10}$ alkyl, and optionally substituted C$_3$-C$_{12}$ cycloalkyl, and
p is 0 to 10.

8. The polymerizable composition of claim 1 further comprising at least one thio(meth)acrylate functional monomer represented by the following Formula (II),

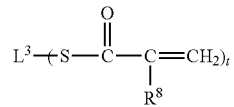

(II)

wherein,
L$^3$ is a multivalent optionally substituted hydrocarbyl group optionally interrupted with at least one of —C(O)—, —S—, —O— and combinations thereof,
R$^8$ is independently selected for each t from hydrogen and methyl, and
t is from 2 to 6.

9. The polymerizable composition of claim 8 wherein,
L$^3$ is selected from multivalent linear or branched optionally substituted C$_1$-C$_{25}$ alkyl, multivalent optionally substituted C$_3$-C$_{12}$ cycloalkyl, multivalent optionally substituted aryl, and combinations thereof optionally interrupted with at least one of —C(O)—, —S—, —O— and combinations thereof.

10. The polymerizable composition of claim 1 wherein,
L$^4$ is selected from multivalent linear or branched optionally substituted C$_1$-C$_{25}$ alkyl, multivalent optionally substituted C$_3$-C$_{12}$ cycloalkyl, multivalent optionally substituted aryl, and combinations thereof optionally interrupted with at least one of —C(O)—, —S—, —O— and combinations thereof, and
L$^5$ is independently for each u selected from divalent linear or branched optionally substituted C$_1$-C$_{25}$ alkyl, divalent optionally substituted C$_3$-C$_{12}$ cycloalkyl, divalent optionally substituted aryl and combinations thereof.

11. The polymerizable composition of claim 1, wherein said polymerization moderator is present and comprises at least one of, 1-isopropyl-4-methyl-1,4-cyclohexadiene; 1-isopropyl-4-methyl-1,3-cyclohexadiene, 1-methyl-4-(propan-2-ylidene)cyclohex-1-ene; 2,6-dimethyl-2,4,6-octatriene, and alpha-methyl styrene dimer.

12. The polymerizable composition of claim 1, further comprising a free radical initiator that is thermally activated.

13. The polymerizable composition of claim 12, wherein said free radical initiator is selected from organic peroxy compounds, azobis(organonitrile) compounds, N-acyloxyamine compounds, O-imino-isourea compounds, and combinations thereof.

14. The polymerizable composition of claim 13, wherein said free radical initiator is selected from at least one organic peroxy compound.

15. The polymerizable composition of claim 14, wherein said free radical initiator comprises at least one of 2,5-dimethyl-2,5-di(2-ethylhexanoylperoxy)hexane, and 1,1-bis(tert-butylperoxy)-3,3,5-trimethylcyclohexane.

16. The polymerizable composition of claim 13, wherein said free radical initiator is selected from at least one of 1-acetoxy-2,2,6,6-tetramethylpiperidine, and 1,3-dicyclohexyl-O—(N-cyclohexylideneamino)-isourea.

17. A polymerizable composition comprising:
(a) at least one first (meth)acrylate functional monomer represented by the following Formula (I),

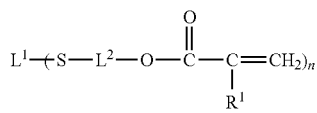  (I)

wherein, n is 2, $L^1$ is represented by the following Formula (B),

  (B)

wherein, $R^2$ for each p is independently selected from linear or branched optionally substituted $C_1$-$C_{10}$ alkyl, and optionally substituted $C_3$-$C_{12}$ cycloalkyl, $R^3$ is selected from linear or branched optionally substituted $C_1$-$C_{10}$ alkyl, and optionally substituted $C_3$-$C_{12}$ cycloalkyl, and p is 0 to 10, $L^2$ is independently for each n a divalent optionally substituted hydrocarbyl group optionally interrupted with at least one of —O— and —S—, and $R^1$ is independently selected for each n from hydrogen and methyl;

(b) at least one second (meth)acrylate functional monomer represented by the following Formula (III),

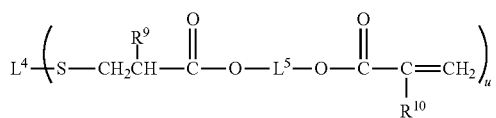  (III)

wherein, $L^4$ is a multivalent optionally substituted hydrocarbyl group optionally interrupted with at least one of —C(O)—, —S—, —O— and combinations thereof, $L^5$ is independently for each u a divalent optionally substituted hydrocarbyl group, $R^9$ and $R^{10}$ are each independently selected for each u from hydrogen and methyl, and u is from 2 to 6;

(c) a polymerization moderator comprising at least one of 1-isopropyl-4-methyl-1,4-cyclohexadiene, 1-isopropyl-4-methyl-1,3-cycloheadiene, 1-methyl-4-(propan-2-ylidene)cyclohex-1-ene, 2,6-dimethyl-2,4,6-octatriene, and alpha-methyl styrene dimer; and (d) optionally, at least one monoethylenically unsaturated monomer.

18. The polymerizable composition of claim 17 wherein, $L^2$ is represented by the following Formula (C),

  (C)

wherein, $R^4$ for each p is independently selected from linear or branched optionally substituted $C_1$-$C_{10}$ alkyl, and optionally substituted $C_3$-$C_{12}$ cycloalkyl, $R^5$ is selected from linear or branched optionally substituted $C_1$-$C_{10}$ alkyl, and optionally substituted $C_3$-$C_{12}$ cycloalkyl, and q is 0 to 10.

19. The polymerizable composition of claim 18 further comprising a free radical initiator that is thermally activated.

20. The polymerizable composition of claim 19, wherein said free radical initiator comprises at least one of 2,5-dimethyl-2,5-di(2-ethylhexanoylperoxy)hexane, and 1,1-bis(tert-butylperoxy)-3,3,5-trimethylcyclohexane.

21. The polymerizable composition of claim 19, wherein said free radical initiator is selected from at least one of 1-acetoxy-2,2,6,6-tetramethylpiperidine, and 1,3-dicyclohexyl-O—(N-cyclohexylideneamino)-isourea.

22. A polymerizable composition comprising:

(a) at least one (meth)acrylate functional monomer represented by the following Formula (IV),

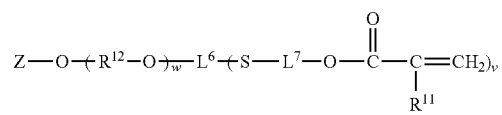  Formula (IV)

wherein, $L^6$ is selected from a multivalent optionally substituted hydrocarbyl group, $L^7$ is independently for each v a divalent optionally substituted hydrocarbyl group optionally interrupted with at least one of —O— and —S—, $R^{11}$ is independently selected for each v from hydrogen and methyl, v is from 2 to 6, $R^{12}$ is independently for each w divalent optionally substituted hydrocarbyl, w is 0 to 10, Z is selected from hydrogen or a group represented by the following Formula (V),

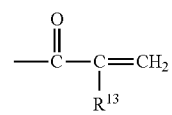  Formula (V)

wherein $R^{13}$ is hydrogen or methyl;

(b) optionally, a polymerization moderator; and (c) optionally, at least one monoethylenically unsaturated monomer.

23. The polymerizable composition of claim 22, wherein, $L^6$ is selected from multivalent linear or branched optionally substituted $C_1$-$C_{25}$ alkyl, multivalent optionally substituted $C_3$-$C_{12}$ cycloalkyl, multivalent optionally substituted aryl, and combinations thereof, $L^7$ is independently for each n selected from divalent optionally substituted linear or branched $C_1$-$C_{25}$ alkyl, divalent optionally substituted $C_3$-$C_{12}$ cycloalkyl, divalent optionally substituted aryl, and combinations thereof optionally interrupted with at least one of —O— and —S—, and $R^{12}$ for each w is independently selected from linear or branched optionally substituted $C_1$-$C_{10}$ alkyl, and optionally substituted $C_3$-$C_{12}$ cycloalkyl.

24. The polymerizable composition of claim 22, further comprising, at least one further (meth)acrylate functional monomer represented by the following Formula (I),

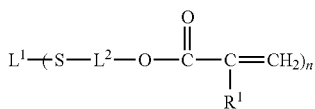

(I)

wherein,

L¹ is a multivalent optionally substituted hydrocarbyl group optionally interrupted with at least one of —C(O)—, —S—, —O— and combinations thereof, L² is independently for each n a divalent optionally substituted hydrocarbyl group optionally interrupted with at least one of —O— and —S—, R¹ is independently selected for each n from hydrogen and methyl, and n is from 2 to 6, provided that L¹ is free of substitution with a group represented by the following Formula (M),

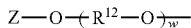

(M)

wherein $R^{12}$, w and Z are each as defined in claim 22.

25. A polymerizable composition comprising:

(a) at least one (meth)acrylate functional monomer represented by the following Formula (I),

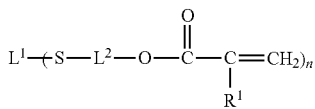

(I)

wherein, n is 2, each R¹ is independently selected from hydrogen and methyl,

L¹ is selected from, (i) a divalent linking group represented by the following Formula (D),

—C(R⁶)(R⁷)— (D)

wherein R⁶ and R⁷ are each independently selected from hydrogen, linear or branched optionally substituted $C_1$-$C_{10}$ alkyl, and optionally substituted $C_3$-$C_{12}$ cycloalkyl, or R⁶ and R⁷ together form a $C_4$-$C_{12}$ optionally substituted cycloalkyl, and (ii) a divalent linking group represented by the following Formula (A),

(A)

wherein Y is O or S, and (iii) L² is represented by the following Formula (B),

—(R²—S)ₚ—R³— (B)

wherein,

R² for each p is independently selected from linear or branched optionally substituted $C_1$-$C_{10}$ alkyl, and optionally substituted $C_3$-$C_{12}$ cycloalkyl, R³ is selected from linear or branched optionally substituted $C_1$-$C_{10}$ alkyl, and optionally substituted $C_3$-$C_{12}$ cycloalkyl, and p is 0 to 10;

(b) at least one second (meth)acrylate functional monomer represented by the following Formula (III),

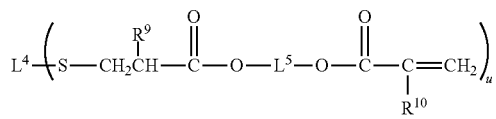

(III)

wherein,

L⁴ is a multivalent optionally substituted hydrocarbyl group optionally interrupted with at least one of —C(O)—, —S—, —O— and combinations thereof, L⁵ is independently for each u a divalent optionally substituted hydrocarbyl group, R⁹ and R¹⁰ are each independently selected for each u from hydrogen and methyl, and u is from 2 to 6;

(c) optionally, a polymerization moderator; and (d) optionally, at least one monoethylenically unsaturated monomer.

26. A polymerizate of the polymerizable composition of claim 1.

27. A polymerizate of the polymerizable composition of claim 4, wherein said polymerizate has a refractive index of at least 1.57, an ABBE number of at least 30, and a Fischer microhardness of at least 50.

28. A photochromic article comprising:

(a) a polymerizate of the polymerizable composition of claim 1; and (b) a photochromic amount of an organic photochromic material.

29. An optical element comprised of the polymerizate of the polymerizable composition of claim 25.

30. An optical element comprised of the polymerizate of the polymerizable composition of claim 1.

31. The optical element of claim 29 further comprising a polarizer.

32. The optical element of claim 30 further comprising a polarizer.

* * * * *